US012584165B2

(12) United States Patent
Stern et al.

(10) Patent No.: US 12,584,165 B2
(45) Date of Patent: Mar. 24, 2026

(54) METHOD FOR IDENTIFYING ONE OR MORE MUTATIONS IN A HOTSPOT MUTATION SEQUENCE

(71) Applicants: Universite de Versailles Saint-Quentin-en-Yvelines, Versailles (FR); Universite de Paris, Paris (FR); Institut National de la Santé et de la Recherche Médicale, Paris (FR); Institut Curie, Paris (FR)

(72) Inventors: Marc-Henri Stern, Paris (FR); Emmanuelle Jeannot, Meudon (FR); Charlotte Proudhon, Pantin (FR); Jean-Yves Pierga, Paris (FR); François-Clément Bidard, Paris (FR)

(73) Assignees: Universite de Versailles Saint-Quentin-en-Yvelines, Versailles (FR); Université Paris Cité, Paris (FR); Institut National de la Santé et de la Recherche Médicale, Paris (FR); Institut Curie, Paris (FR)

( * ) Notice: Subject to any disclaimer, the term of this patent is extended or adjusted under 35 U.S.C. 154(b) by 1224 days.

(21) Appl. No.: 16/980,657

(22) PCT Filed: Mar. 14, 2019

(86) PCT No.: PCT/EP2019/056445
§ 371 (c)(1),
(2) Date: Sep. 14, 2020

(87) PCT Pub. No.: WO2019/175323
PCT Pub. Date: Sep. 19, 2019

(65) Prior Publication Data
US 2021/0024984 A1 Jan. 28, 2021

(30) Foreign Application Priority Data

Mar. 14, 2018 (EP) ...................................... 18305277

(51) Int. Cl.
*C12Q 1/6858* (2018.01)
*C12Q 1/6818* (2018.01)
*C12Q 1/6886* (2018.01)

(52) U.S. Cl.
CPC ......... *C12Q 1/6858* (2013.01); *C12Q 1/6818* (2013.01); *C12Q 1/6886* (2013.01); *C12Q 2600/106* (2013.01); *C12Q 2600/156* (2013.01)

(58) Field of Classification Search
CPC ................ C12Q 1/6858; C12Q 1/6818; C12Q 2561/101; C12Q 2563/159; C12Q 2537/143; C12Q 1/6827
See application file for complete search history.

(56) References Cited

PUBLICATIONS

Jeselsohn et al. ESR1 mutations—a mechanism for acquired endocrine resistance in breast cancer. Nature Reviews Clinical Oncology 2015; 12: 573-583 (Year: 2015).*

(Continued)

*Primary Examiner* — Angela M. Bertagna
(74) *Attorney, Agent, or Firm* — Morgan, Lewis & Bockius LLP

(57) ABSTRACT

The present invention relates to an in vitro method for identifying and/or characterizing one or more mutations in a hotspot mutation sequence of at least one ESR1 target fragment from a DNA sample, with a drop-off digital polymerase chain reaction (PCR).

14 Claims, 5 Drawing Sheets

Figure 1:
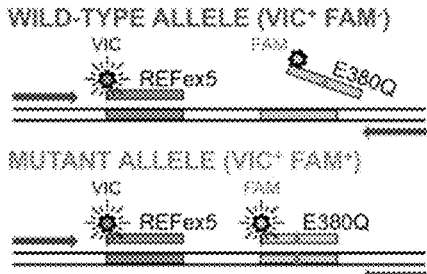
Figure 1:
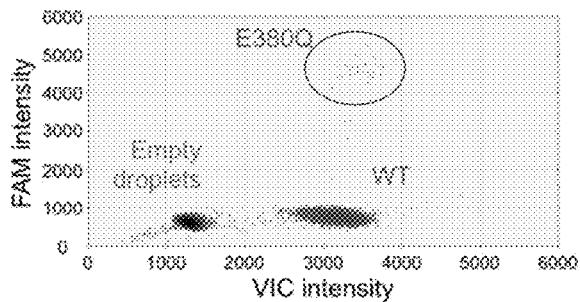
Figure 1:
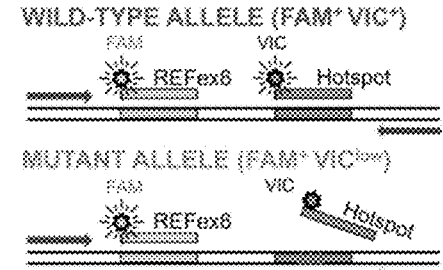
Figure 1:
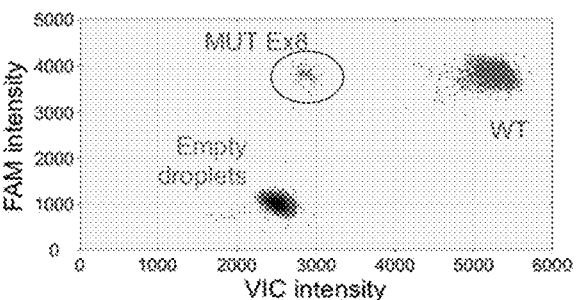
Figure 1:
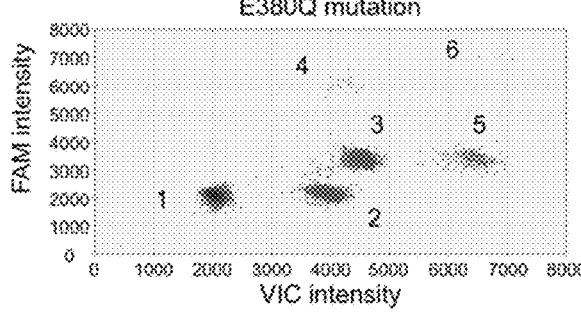
Figure 1:
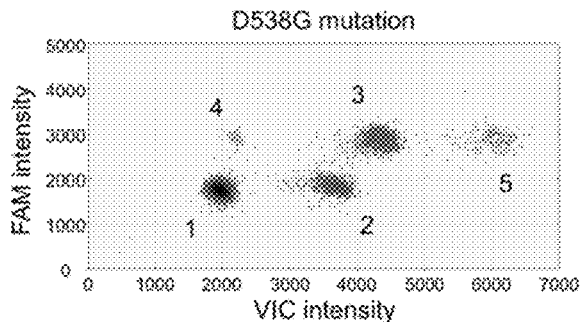

Specification includes a Sequence Listing.

(56) References Cited

PUBLICATIONS

Decraene et al. Multiple Hotspot Mutations Scanning by Single Droplet Digital PCR. Clinical Chemistry 2018; 64: 317-328 (Year: 2018).*

Schiavon et al. Analysis of ESR1 mutation in circulating tumor DNA demonstrates evolution during therapy for metastatic breast cancer. Science Translational Medicine 2015; 7: 313ra182 (Year: 2015).*

Bidshahri et al. Quantitative detection and resolution of BRAF V600 status in colorectal cancer using droplet digital PCR and a novel wild-type negative assay. The Journal of Molecular Diagnostics 2016; 18: 190-204 (Year: 2016).*

Yung et al. Single-Molecule Detection of Epidermal Growth Factor Receptor Mutations in Plasma byMicrofluidics Digital PCR in Non-Small Cell Lung Cancer Patients. Clinical Cancer Research 2009; 15: 2076-2084 (Year: 2009).*

Jeannot et al. A single droplet digital PCR for ESR1 activating mutations detection in plasma. Oncogene 2020; 39: 2987-2995 (Year: 2020).*

Alcaide et al. Multiplex Droplet Digital PCR Quantification of Recurrent Somatic Mutations in Diffuse Large B-Cell and Follicular Lymphoma. Clinical Chemistry 2016; 62: 1238-1247 (Year: 2016).*

Madic et al. EGFR C797S, EGFR T790M and EGFR sensitizing mutations in non-small cell lung cancer revealed by six-color crystal digital PCR. Oncotarget 2018; 9: 37393-37406 (Year: 2018).*

Schiavon et al. Analysis of ESR1 mutation in circulating tumor DNA demonstrates evolution during therapy for metastatic breast cancer. Science Translational Medicine 2015; 7: 313ra182 + Supplementary Table 2 (Year: 2015).*

International Search Report issued in corresponding International Patent Application No. PCT/EP2019/056445 dated Jun. 17, 2019.

Written Opinion issued in corresponding International Patent Application No. PCT/EP2019/056445 dated Jun. 17, 2019.

* cited by examiner

A    E380Q assay (Exon 5)

B    Drop-off Ex8 assay (Exon 8)

C    Multiplex assay (Exon 5 + Exon 8)

METHOD FOR IDENTIFYING ONE OR MORE MUTATIONS IN A HOTSPOT MUTATION SEQUENCE

SEQUENCE LISTING SUBMISSION

A computer readable text file, entitled 118907-5067 ST25.txt created on Sep. 8, 2025 with a file size of 3,000 bytes contains the sequence listing for this application and is hereby incorporated by reference in its entirety.

INTRODUCTION

In most breast cancer cases, the estrogen receptor (ER) is exerting a key survival signaling, and ER-positive immunostaining is a well characterized predictive biomarker of hormone therapy activity at both early and advanced stages.

Four main types of endocrine therapy are classically used for breast cancer: (1) selective ER modulators (such as tamoxifen), (2) selective ER downregulators (such as fulvestrant), (3) aromatase inhibitors (Als, which include anastrozole, létrozole or exemestane), and (4) gonadotropin-releasing hormone agonists. Although most hormone receptor (HR)-positive patients can benefit from these drugs, during endocrine therapy, endocrine resistance is common and essentially inevitable in advanced disease stages. Indeed, estrogen synthesis is the main therapeutic target for over 70% of breast cancer that feature estrogen receptor expression. Such treatments markedly reduce the risk of recurrence from early-stage disease and improve outcomes in those with advanced disease. However, despite this efficacy, a significant subset of estrogen receptor positive (ER+) breast tumors ultimately develops resistance to antiestrogen therapy.

In 2013, a couple of studies reported recurrent activating point mutations in ESR1, the gene encoding for the Estrogen Receptor (ER)α subunit (Toy W et al., "ESR1 ligand-binding domain mutations in hormone-resistant breast cancer." Nat Genet. 2013 December; 45(12):1439-45 Robinson et al., 'Activating ESR1 mutations in hormone-resistant metastatic breast cancer." Nat Genet. 2013 December; 45(12):1446-51). These mutations were shown oncogenic, to activate ERα in a ligand-independent manner and were proposed as a potential mechanism of breast cancer resistance to hormone depletion (by e.g. aromatase inhibitors).

The majority of ESR1 mutations occur in the ESR1 ligand binding domain (LBD) "hot spot" regions that is confined to codons 537 and 538 in exon 8. To date, there are twelve known hot spot mutations that have been described. Among these mutations, the most frequent are Y537S, Y537N, Y537C, and D538G, which cover more than 80% of ESR1 mutations and are clustered in the LBD. Other mutations, including L536Q, L536R, P535H, V534E, K303R, S463P, and E380Q, at other positions have also been described (See Weiyi Toy et al., "*Activating ESR1 Mutations Differentially Affect the Efficacy of ER Antagonists*" Cancer Discov Mar. 1, 2017 (7) (3):277-287). Forty percent of patients had more than one ESR1 mutation, and in rare cases, patients had as many as four or five detectable, low-frequency ESR1 mutations The majority of ESR1 mutations occur in exon 8 corresponding to hotspot regions within the ligand-binding domain (LBD) of ER, altering codons 536, 537, and 538 in helix 12 (the most frequent including p.Leu536Arg, p.Tyr537Ser, p.Tyr537Asn, p.Tyr537Cys, and p.Asp538Gly) (8-11) (Schiavon G et al., Analysis of ESR1 mutation in circulating tumor DNA demonstrates evolution during therapy for metastatic breast cancer. Science Translational Medicine. 2015; 7(313):313ra182, Toy et al., Cancer Discovery 2017). Other mutations, including L536Q and L536R have also been described Functional studies of these LBD ESR1 mutations demonstrated that they constitutively activate the ER in a ligand-independent fashion. Hence cancers with these ESR1 mutations would be predicted to be resistant to Als and ovarian suppression in premenopausal women, because these therapies work by depriving ligand. In contrast, in vitro and in vivo, LBD ESR1 mutations retain limited sensitivity to tamoxifen and fulvestrant (a selective ER modulator and a selective ER down-regulator, respectively) Another hotspot mutation region is located in exon 5 and corresponds to the codon 380, the most frequent mutation corresponding to E380Q.

ESR1 mutations are generally selected frequently during treatment for metastatic breast cancer, likely through selection of rare ESR1 mutant sub-clones that were present in low amounts before therapy as a result of genetic intra-tumoral heterogeneity and clonal diversity in the cancer (Schiavon G et al., 2015).

Although these ESR1 mutations are rarely detected in primary tumors and at first metastatic relapse, their overall incidence increases alongside the exposure of patients to aromatase inhibitors in ER-positive HER2-negative metastatic breast cancer patients, likely through selection of rare ESR1 mutant sub-clones that were present in low amounts before therapy as a result of genetic intra-tumoral heterogeneity and clonal diversity in the cancer (Schiavon G et al., 2015). It has been reported that 30 to 40% of aromatase inhibitor-resistant ER-positive HER2-negative MBC patients display ESR1 mutations, some patients harboring polyclonal ESR1 mutations (Chandarlapaty S et al., "Prevalence of ESR1 Mutations in Cell-Free DNA and Outcomes in Metastatic Breast Cancer: A Secondary Analysis of the BOLERO-2 Clinical Trial. JAMA Oncol. 2016 Oct. 1; 2(10):1310-1315).

Patients with ESR1 mutations had a substantially shorter progression-free survival on subsequent AI-based therapy. However, other hormone therapy agents such as selective ER down-regulators (e.g. fulvestrant) retains a significant activity on mutated estrogen receptor (Toy W et al., 2017), suggesting that ESR1 mutations could be a predictive biomarker in the management of ER-positive metastatic breast cancers (Fribbens C et al., "Mutations and the Treatment of Estrogen Receptor-Positive Advanced Breast Cancer". J Clin Oncol. 2016 Sep. 1; 34(25):2961-8.).

Accurate and sensitive detection tools are therefore needed to initiate clinical trials investigating the utility of ESR1 mutation detection.

Prior researches have demonstrated that circulating tumor DNA (ctDNA) is detected in the plasma of patients with cancer and may thus provide a robust and non-invasive method for detecting ESR1 mutations. Additionally, such a liquid biopsy potentially affords an invaluable approach for longitudinal measurement of mutations, to optimally guide therapy that is simply not possible with solid biopsies. Yet, serial biopsies of recurrent, metastatic cancer would be invasive, risky, and unacceptable to many patients (5).

Tests assessing ESR1 mutation(s) based on multiplex droplet digital PCR have been recently described (see Schiavon G et al., 2015; Fribbens et al., 2016).

These assays, which involve one probe per mutation, remain however quite complex. Indeed, the concentration of each probe has to be carefully adjusted to differentiate mutations, and at least two multiplex assays have to be run in order to detect the most frequent ESR1 mutations. Typically in Fribbens et al., samples were screened using two multiplex assays. Furthermore, characterization of the mutation(s), if the multiplex is positive, is only achieved by uniplex ddPCR assays. Large sample amounts are therefore required for adequate characterization of ESR1 mutations.

Also, the current studies that used ddPCR as a detection method only queried for the most common ESR1 LBD mutations, (typically D538G, Y537N, and Y537S), it is therefore likely that less frequent mutations associated with endocrine therapy resistance be missing.

Thus, while multiplexed assays have been developed to reduce the number of reactions, these assays cannot identify more than 4 ESR1 mutations in a single reaction and the mutant samples had to be confirmed by singleplex tests. More generally, the relatively high costs associated with such tests may limit the clinical use of ESR1 mutation monitoring methods.

It is thus of high relevance to develop sensitive and specific new assays, which allows detection and characterization of the ESR1 mutations in a DNA sample, which can be easily implemented and at low costs.

SUMMARY

The present invention relates to an in vitro method for identifying and/or characterizing one or more mutations in a hotspot mutation sequence of at least one target fragment from a DNA sample.

The method of the invention is characterized in that it comprises subjecting the DNA sample to a drop-off digital polymerase chain reaction (PCR) in the presence of a PCR solution comprising:

a pair of primers suitable for amplifying the at least one target fragment (including the hotspot mutation sequence);

an oligonucleotide reference (REF) hydrolysis probe, labeled with a fluorophore, wherein said REF oligonucleotide probe is complementary to a wild-type sequence of the target fragment located outside of the hotspot mutation sequence;

an oligonucleotide hotspot (HOTSPOT) hydrolysis probe, labeled with another fluorophore, wherein said oligonucleotide HOTSPOT probe is complementary to a wild-type sequence of the hotspot mutation sequence of the target DNA fragment.

Indeed, using an original drop-off droplet digital PCR (ddPCR) design, the inventors set up an assay that can sensitively and specifically detect more than 80% of the activating ESR1 mutations in circulating DNA, by targeting mutations at codons 380, 536, 537 and 538.

They demonstrated that drop-off ddPCR, is a well indicated approach for both screening and/or characterization of hotspot mutations and notably ESR1 hotspot mutations.

Unlike, conventional ddPCR, which requires a probe for each mutation, the drop-off assay uses a single hydrolysis probe (i.e.: TaqMan® probe) for detecting all the mutations clustered in the hotspot. Surprisingly, and contrary to all expectations, the inventors have now discovered that such drop of assay not only allow (i) to identify the presence or not of mutation(s) in the hotspot sequence but also (ii) to discriminate or characterize each specific mutation, based on the shifted position of the droplet cloud for each mutation. Using such approach, the inventors were for example able to detect with a single probe and in a single assay, the majority of the mutations in the hotspot region corresponding to codons 536-538 of ESR1. The results presented herein show that the method of the invention is of high relevance for the identification and monitoring of mutant clones (typically in breast cancer and more particularly in breast cancer associated with ESR1 mutations.). Indeed, in such context, the method of the invention allows early adaptation of the treatment as a function of the mutations which have been identified and/or characterized. The present invention may help avoid or limit development of metastasis associated with treatment resistance.

Such approach, which preserves the sensitivity and specificity of ddPCR, now provides a significant improvement as the mutations from a hotspot region can be easily characterized in one step using a single HOTSPOT probe together with a reference probe. The amount of DNA sample to be used is kept minimal. Lastly the cost associated with such method should be reduced as compared to current ddPCR technique and may allow developing routine clinical monitoring of hotspot mutations and more particularly of ESR1 hotspot mutation(s).

Thus more particularly, the present invention relates to an in vitro method for identifying and characterizing one or more mutations in a hotspot mutation sequence of at least one ESR1 target fragment from a DNA sample.

The method of the invention is characterized in that is comprises subjecting the DNA sample to a drop-off digital polymerase chain reaction (PCR) in the presence of a PCR solution comprising:

a pair of primers suitable for amplifying an ESR1 target fragment (including the hotspot mutation sequence);

an oligonucleotide reference (REF) hydrolysis probe, labeled with a fluorophore, wherein said REF oligonucleotide probe is complementary to a wild-type sequence of the target fragment located outside of the hotspot mutation sequence;

an oligonucleotide hotspot (HOTSPOT) hydrolysis probe, labeled with another fluorophore, wherein said oligonucleotide HOTSPOT probe is complementary to a wild-type sequence of the hotspot mutation sequence of the target DNA fragment.

Typically, the target DNA fragment is from the ligand binding domain of the estrogen receptor. More particularly, the target fragment of the DNA sample is exon 8. In a preferred embodiment, the hotspot mutation sequence includes codons 536-538 of exon 8.

In a preferred embodiment, the drop-off digital PCR of the invention is combined (i.e.: duplexed) with a non-conventional mutation specific ddPCR for identifying a mutation in a further hotspot mutation sequence of a further target fragment from said DNA sample.

Typically, the PCR solution therefore further comprises:

a pair of primers suitable for amplifying said further target fragment of the DNA sample;

an oligonucleotide hydrolysis probe (MS-MUT), labeled with a fluorophore, wherein said oligonucleotide MUT probe is complementary to the hotspot mutation sequence of said second target fragment.

an oligonucleotide reference (MS-REF) hydrolysis probe, labeled with another, wherein MS-REF oligonucleotide probe is complementary to a wild-type sequence of said second target fragment located outside of the hotspot mutation sequence.

More particularly, the target fragment is from ESR1, notably the further target fragment is exon 5. Typically said further target fragment includes codon 380.

This multiplex test detects, in a single reaction, up to 95% of the described activating ESR1 mutations, based on previous studies and is compatible with body fluid samples.

Typically, the one or more target fragments are from genomic tumor DNA.

The present invention also relates to an in vitro method for the monitoring of ESR1 mutations, for the prognosis of breast cancers, or for predicting the efficacy of a treatment endocrine therapy for breast cancer in a subject suffering from a cancer, wherein the method according to any one of the preceding claims is performed on a DNA sample from a subject during the time course of the treatment.

The present invention also comprises a kit for the characterization of ESR1 hotspot mutations in a target fragment from a DNA sample, wherein the kit comprises:

a pair of primers suitable for amplifying an ESR1 target fragment (including the hotspot mutation sequence);

an oligonucleotide reference (REF) hydrolysis probe, labeled with a fluorophore, wherein said REF oligonucleotide probe is complementary to a wild-type sequence of the target fragment located outside of the hotspot mutation sequence;

an oligonucleotide hotspot (HOTSPOT) hydrolysis probe, labeled with another fluorophore, wherein said oligonucleotide HOTSPOT probe is complementary to a wild-type sequence of the hotspot mutation sequence of the target DNA fragment; and a thermostable polymerase.

In one embodiment, the kit may further comprise:

a pair of primers suitable for amplifying said second ESR1 target fragment of the DNA sample;

an oligonucleotide hydrolysis probe (MS-MUT), labeled with a fluorophore, wherein said oligonucleotide MUT probe is complementary to the hotspot mutation sequence of said second target fragment.

an oligonucleotide reference (MS-REF) hydrolysis probe, labeled with another fluorophore, wherein MS-REF oligonucleotide probe is complementary to a wild-type sequence of said second target fragment located outside of the hotspot mutation sequence.

DETAILED DESCRIPTION

To the Applicant knowledge, the present disclosure is the first to propose a ddPCR assay which can detect, in a single reaction, at least eight different mutations in ESR1, namely: E380Q, L536H, L536R, Y537C, Y537N (T>A), Y537N (delinsTA), Y537S and D538G.

In addition, the method as herein disclosed can identify samples harboring multiple ESR1 mutations (e.g., E380Q combined with one or more mutations in exon 8). Polyclonal ESR1 mutations are well-described events and the ESR1-ddPCR assay is of particular clinical relevance for monitoring the dynamics of each mutation during treatment follow up as seen for P-43.

The multiplex ESR1-ddPCR assay, notably the combined multiplex assay as herein as herein described is highly sensitive, and is able to detect all tested mutations at frequencies lower than 0.19%, which is a significant an improvement as compared with next generation sequencing method (NGS). ESR1-ddPCR is highly specific as demonstrated by cross-validation with NGS experiments.

Lupini et al. («High-sensitivity assay for monitoring ESR1 mutations in circulating cell-free DNA of breast cancer patients receiving endocrine therapy». Sci Rep; 8(1): 4371) recently developed an assay based on an "enhanced-ice-COLD-PCR followed by NGS" with a sensitivity reaching 0.01%. However, this ddPCR assay targets specifically the Y537S mutation and involves an enrichment step of the mutant copies preceding the ddPCR assay. Yet, in a context of patient monitoring by liquid biopsy, biological samples are of limited quantity and must be tested rapidly at a low cost. The multiplex ESR1-ddPCR can detect most ESR1 mutations in a single reaction faster and at a lower cost than NGS or any other currently available technology.

Furthermore, the results herein included clearly show exons 5 and 8 mutations can be easily distinguished. Indeed, among exon 8 mutations, the shift in clouds is unique depending on the mutation, indicating for example if the mutation is more likely to be a D538G or Y537C allele versus mutations in codon 536 or other changes in codon 537.

Preclinical data suggest that the Y537S mutation, which accounts for about 10% of all ESR1 mutations, may be less sensitive to fulvestrant than other mutations, the ESR1-ddPCR assay as herein described could be used as a first screening tool, since the shift associated to Y537S is distinguishable from the most frequent mutation: D538G, followed by subsequent sequencing of exon 8, to distinguish Y537S from other 536/537 mutations.

Lastly, the improved analytical sensitivity of the ESR1-ddPCR is particularly useful to monitor ctDNA during treatment follow-up. The inventors demonstrated that ESR1 mutations are good markers for ctDNA dynamics exploration and prediction of treatment response. Indeed, the inventors observed that detection of ctDNA after 30 days of palbociclib-fulvestrant, using the ESR1-ddPCR, correlates with the treatment response and has an impact on PFS.

Definitions

The following definitions are intended to assist in providing a clear and consistent understanding of the scope and detail of the following terms, as used to describe and define the present invention:

As used herein, the verb "comprise" and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one."

As used herein a "tumor" or a "neoplasm" (both terms can be used interchangeably) is an abnormal new growth of cells. The cells in a neoplasm usually grow more rapidly than normal cells and will continue to grow if not treated. As they grow, neoplasms can impinge upon and damage adjacent structures. The term neoplasm can refer to benign (usually curable) or malignant (cancerous) growths.

A benign tumor, or neoplasm, is usually localized, and does not spread to other parts of the body. Most benign tumors respond well to treatment. However, if left untreated, some benign tumors can grow large and lead to serious disease because of their size. Benign tumors can also mimic malignant tumors, and so for this reason are sometimes treated.

Malignant tumors are cancerous growths. They are often resistant to treatment, may spread to other parts of the body (i.e. metastasis) and they sometimes recur after they were removed.

The term "cancer" is used herein for a malignant tumor.

"Allele", as used herein, refers to one of several alternative forms of a gene or DNA sequence at a specific chromosomal location (locus). At each autosomal locus an individual possesses two alleles, one inherited from the father and one from the mother.

"DNA polymorphism", as used herein, refers to the existence of two or more alleles for a given locus in the population. "Locus" or "genetic locus", as used herein, refers to a unique chromosomal location defining the position of an individual gene or DNA sequence. "Locus-specific primer", as used herein, refers to a primer that specifically hybridizes with a portion of the stated locus or its complementary strand, at least for one allele of the locus, and does not hybridize efficiently with other DNA sequences under the conditions used in the amplification method.

As used herein, a "primer/probe set" refers to a grouping of a pair of oligonucleotide primers and two oligonucleotide probes that each hybridizes to a specific target nucleotide sequence. Said oligonucleotide set consists of: (a) a forward discriminatory primer that hybridizes to a first location of a nucleic acid sequence; (b) a reverse discriminatory primer that hybridizes to a second location of the nucleic acid sequence downstream of the first location and (c) two probes, which hybridizes to a target sequence between the primers. In other words, a primer/probe set consists of a pair of specific oligos that anneal to opposite strands of a nucleic acid sequence (typically including a hotspot sequence locus) so as to form an amplicon specific to the nucleic acid sequence during the PCR reaction, and two probes, preferably fluorescent (typically hydrolysis probes), which hybridize to (i.e., which are complementary to) a specific target sequence of the amplicon.

An "amplicon" refers to a nucleic acid fragment formed as a product of natural or artificial amplification events or techniques. Typically, the amplicon is produced by Polymerase chain reaction (PCR). "Amplifying", as used herein, refers to a process whereby multiple copies are made of one particular locus of a nucleic acid (i.e. a target sequence as mentioned above), such as genomic DNA. Amplification is accomplished using PCR (Saiki et al., 1985 Science 230: 1350-1354).

An oligonucleotide hydrolysis probe (also simply named "hydrolysis probe", "TaqMan probe" or "exonuclease probe") is sequence specific. These dual labeled probes hybridize to a target sequence, internal to the primers and include one fluorescent reporter and one quencher. The fluorescence from exonuclease probes results from probe cleavage by 5'-exonuclease activity.

A "target (DNA) fragment", or a "target (DNA) region" used interchangeably herein relates to the fragment of the DNA sample that is amplified by a pair of primers of a primer/probe set. According to the invention, such target fragment includes hotspot mutation region.

A "target sequence", or "target DNA sequence" used interchangeably refers to a DNA sequence which is complementary to one or the other oligonucleotide probe (typically which is complementary to the REF probe or to the HOT-SPOT probe).

A "hotspot region" (also named herein "hotspot sequence" or "hotspot mutation sequence") is a region from the genome that exhibit elevated rates of recombination relative to a neutral expectation.

Detection of genetic alteration in the field of cancerology, virology or prenatal diagnostic requires an exceptionally high level of both sensitivity and specificity, which cannot be obtained with conventional techniques. Digital PCR combines dilution end-point of the DNA sample, PCR and Poisson distribution. The dPCR approach involves serial dilution of the sample in order to obtain end-point dilution of the sample wherein each partition contains at most one target DNA molecule. Statistic distribution of DNA in each compartment is thus given by the Poisson Law. Partitions are thus submitted to PCR amplification and analyzed individually. The signal obtained by the detection of minority markers of the sample can thus be detected. By performing amplifications of single DNA molecules into independent compartments, digital PCR (dPCR) thus allows to overcome this limitation and to monitor those genetic markers into biological fluids. Digital PCT is therefore particularly relevant for the detection and the quantification of minority markers such as sub-clones from complex DNA mixtures in tumors or in circulating DNA.

The digital PCR concept has also the advantage over RT-PCR, to allow obtaining absolute quantification without external references and robustness to variations in PCR efficiency.

As used herein, "digital FOR" refers to an assay that provides an end-point measurement that provides the ability to quantify nucleic acids without the use of standard curves, as is used in real-time PCR (see Sykes et al., 1992 Quantitation of targets for PCR by use of limiting dilution. BioTechniques 13, 444-449, Vogelstein and Kinzler 1999 Digital PCR. Proc Natl Acad Sci USA, 96:9236-9241 and Pohl and Shihle 2004 Principle and applications of digital PCR. Expert Rev Mol Diagn, 4:41-47, see also Monya Baker 2012 Nature Methods 9, 541-544).

In a typical digital PCR experiment, a PCR solution is made similarly to a classical TaqMan probe assay, which typically comprises the DNA sample, fluorescence-quencher probes (i.e., hydrolysis probes or TaqMan probes as defined above), primers, and a PCR master mix, which generally contains DNA polymerase, dNTPs, $MgCl_2$, and reaction buffers at optimal concentrations. The PCR solution is then randomly distributed into discrete (i.e. individual) partitions or compartments, such that some contain no target DNA and others contain one or more target DNA copies, most preferably one target DNA copy. Thus, in these conditions, the reference signal associated with the presence of the target DNA in the DNA sample in a given partition or compartment should be theoretically 0 or 1. Obviously due to biological variability for a population of partition or compartment, clouds are observed corresponding respectively to the theoretic values 0 or 1.

The partitions are individually amplified to the terminal plateau phase of PCR (or end-point) and then read for fluorescence, to determine the fraction of positive partitions. If the partitions are of uniform volume, the number of target DNA molecules present may be calculated from the fraction of positive end-point reactions using Poisson statistics, according to the following equation:

$$\lambda=-\ln(1-p) \tag{1}$$

wherein $\lambda$ is the average number of target DNA molecules per replicate reaction and p is the fraction of positive end-point reactions. From $\lambda$, together with the volume of each replicate PCR and the total number of replicates analyzed, an estimate of the absolute target DNA concentration is calculated.

Micro well plates, capillaries, oil emulsion, and arrays of miniaturized chambers with nucleic acid binding surfaces can be used to partition the samples in distinct compartments or droplets. Thus digital PCR as used herein includes a variety of formats, including droplet digital PCR (ddPCR), BEAMing (beads, emulsion, amplification, and magnetic), and microfluidic chips. Techniques available for digital PCR include PCR amplification on a microfluidic chip (Warren et al., 2006 Transcription factor profiling in individual hematopoietic progenitors by digital RT-PCR. Proc Natl Acad Sci USA 103, 17807-17812; Ottesen et al., 2006 Microfluidic digital PCR enables multigene analysis of individual environmental bacteria. Science 314, 1464-1467; Fan and Quake 2007 Detection of aneuploidy with digital polymerase chain reaction. Anal Chem 79, 7576-7579). Other systems involve separation onto microarrays (Morrison et al., 2006 Nanoliter high-throughput quantitative PCR. Nucleic Acids Res 34, e123) or spinning microfluidic discs (Sundberg et al., 2010 Spinning disk platform for microfluidic digital polymerase chain reaction. Anal Chem 82, 1546-1550) and droplet techniques based on oil-water emulsions (Hindson, Benjamin et al., 2011 High-Throughput Droplet Digital PCR System for Absolute Quantitation of DNA Copy Number. Analytical Chemistry 83 (22): 8604-8610). Typically, digital PCR is selected from droplet digital PCR (ddPCR), BEAMing (beads, emulsion, amplification, and magnetic), and microfluidic chips. Preferably, the digital PCR is droplet digital PCR.

"Droplet digital FOR" (ddPCR) refers to a digital PCR assay that measures absolute quantities by counting nucleic acid molecules encapsulated in discrete, volumetrically defined, water-in-oil droplet partitions that support PCR amplification (Hinson et al., 2011, Anal. Chem. 83:8604-8610; Pinheiro et al., 2012, Anal. Chem. 84: 1003-1011). A single ddPCR reaction may be comprised of at least 20,000 partitioned droplets per well.

A "droplet" refers to an individual partition of the PCR solution in a droplet digital PCR assay. In the following of the present application, digital PCR will be described in reference to droplet digital (or digital droplet PCR, used interchangeably), however, as mentioned previously individual partition of the PCR solution according to the principle of digital PCR can be obtained according to a variety of techniques. Therefore, the method of the invention as described below in reference to droplet digital PCR is not limited to this digital PCR technique and may be applied in a similar fashion to other digital PCR techniques.

A droplet supports PCR amplification of template molecule(s) using homogenous assay chemistries and workflows similar to those widely used for real-time PCR applications (Hinson et al., 2011, Anal. Chem. 83:8604-8610; Pinheiro et al., 2012, Anal. Chem. 84:1003-1011). Once droplets are generated, they can be transferred on a PCR plate and emulsified PCR reactions can be run on a thermal cycler under a classical program such as for example described in the Biorad's Guideline for ddPCR [(www.bio-rad.com/webroot/web/pdf/lsr/literature/Bulletin_6407.pdf)].

Droplet digital PCR may be performed using any platform that performs a digital PCR assay that measures absolute quantities by counting nucleic acid molecules encapsulated in discrete, volumetrically defined, water-in-oil droplet partitions that support PCR amplification. The strategy for droplet digital PCR may be summarized as follows: The PCR solution containing the DNA sample is diluted and partitioned into thousands to millions of separate reaction chambers (water-in-oil droplets) so that each contains one or no copies of the nucleic acid molecule of interest.

The number of "positive" droplets detected, which contain the target amplicon (i.e., target DNA fragment) (i.e., according to the present invention REF positive droplets), versus the number of "negative" droplets, which do not contain the target amplicon (i.e., REF negative droplets), may be used to determine the number of copies of the nucleic acid molecule of interest that were in the original sample.

Examples of droplet digital PCR systems include the QX100™ Droplet Digital PCR System by Bio-Rad, which partitions samples containing nucleic acid template into 20,000 nanoliter-sized droplets; and the RainDrop™ digital PCR system by RainDance, which partitions samples containing nucleic acid template into 1,000,000 to 10,000,000 picoliter-sized droplets.

Briefly, the benefits of dPCR and more particularly ddPCR technology include:

Absolute quantification, as ddPCR technology provides an absolute count of target DNA copies per input sample without the need for running standard curves.

Unparalleled precision, as the massive sample partitioning afforded by ddPCR enables the reliable measurement of small fold differences in target DNA sequence copy numbers among samples.

Increased signal-to-noise ratio: high-copy templates and background are diluted, effectively enriching template concentration in target-positive partitions, allowing for the sensitive detection of rare targets.

Removal of PCR bias, as error rates are reduced by removing the amplification efficiency reliance of qPCR, enabling the detection of small (1.2-fold) differences.

Simplified quantification, since neither calibration standards nor a reference required for absolute quantification.

Reduced consumable costs, as reaction volumes are in the pico- to nanoliter ranges, reducing reagent use and the sample quantity required for each data point.

Lower equipment costs, as the emulsion-based reaction system means that the PCR reactions can be performed in a standard thermal cycler without complex chips or microfluidics.

Superior partitioning, since ddPCR technology yields 20,000 droplets per 20 μl sample, nearly two million partitioned PCR reactions in a 96-well plate, whereas chip-based digital PCR systems produce only hundreds or thousands of partitions. The greater number of partitions also yields higher accuracy.

The term "melting temperature" or "Tm" refers to the temperature at which a polynucleotide dissociates from its complementary sequence. Generally the Tm may be defined as the temperature at which one-half of the Watson-Crick base pairs in a duplex nucleic acid molecule are broken or dissociated (i.e. are "melted") while the other half of the Watson-Crick base pair remain intact in a double stranded conformation. In other words, the Tm is defined as the temperature at which 50% of the nucleotides of two complementary sequences are annealed (double strands) and 50% of the nucleotides are denatures (single strands). The Tm can be estimated by a number of methods, such as for example by a nearest-neighbor calculation as per Wetmur 1991 (Wetmur 1991 DNA probes: applications of the principles of nucleic acid hybridization. Crit Rev Biochem Mol Biol 26: 227-259, hereby incorporated by reference) or by commercial programs including Oligo™ Primer Design and programs available on the internet. Alternatively, the Tm can be determined through actual experimentation. For example, double-stranded DNA binding or intercalating dyes, such as ethidium bromide or SYBR-green (Molecular Probes) can be used in a melting curve assay to determine the actual Tm of the nucleic acid.

As used herein, the term "critical denaturation temperature" or "Tc" refers to a temperature below the Tm of the wild type sequence, at which temperature a duplex of the wild-type sequence and the mutant sequence will melt. (In some instances, this temperature may be one at which a homoduplex of the mutant sequences also melts). The critical denaturing temperature (Tc) is the temperature below which PCR efficiency drops abruptly for a given nucleic acid sequence.

Method for the Characterization of One or More Mutations of a Hotspot Mutation Sequence Comprising a Drop-Off dPCR Assay The present invention relates to an in vitro method for identifying and/or characterizing one or more mutations in a hotspot sequence of at least one target fragment from a DNA sample.

The method of the invention is characterized in that is comprises subjecting the DNA sample to a drop-off digital polymerase chain reaction (PCR) in the presence of a PCR solution comprising:

a pair of primers suitable for amplifying the at least one target fragment (including the hotspot sequence);

an oligonucleotide reference (REF) hydrolysis probe, labeled with a fluorophore, wherein said REF oligonucleotide probe is complementary to a wild-type sequence of the target fragment located outside of the hotspot mutation sequence;

an oligonucleotide hotspot (HOTSPOT) hydrolysis probe, labeled with another fluorophore, wherein said oligonucleotide HOTSPOT probe is complementary to a wild-type sequence including the hotspot sequence of the target DNA fragment.

Preferably, the target fragment is an ESR1 fragment including at least one hotspot mutation sequence.

Preferably also, at least one target fragment is from the ligand binding domain of the estrogen receptor, notably the target fragment includes exon 8 and notably includes a hotspot mutation sequence comprising codons 536-538.

The drop off assay according to the invention is based on a single PCR reaction with two hydrolysis probes located within the same amplicon (internal to the primer).

Previous assays showed great sensitivity and reproducibility in detecting hotspot mutations in EGFR, RAS, BRAF genes (Decraene et al, Seki 2016 the Oncologist, Bidshahri et al., The Journal of Molecular Diagnostic 2016, (18):2, 190-204). Unlike conventional ddPCR which requires a probe for each mutation, the drop-off assay uses a single Tag Man® probe for detecting all the mutations clustered in the hotspot. Since a probe needs a perfect match to hybridize its target sequence, the drop-off assay leans on the concept that a single mismatch is enough to destabilize the complex probe-target sequence. Hence, any mutation in the region covered by the probe will lead to a loss of signal compared to wild-type sample. In other words the assay of the invention allows to discriminate virtually all mutations which are covered by the HOTSPOT probe.

The HOTSPOT probe covers the full WT sequence of the hotspot region. Indeed, said HOTSPOT probe typically hybridizes with a wild-type target sequence of the amplified target DNA fragment, which includes hotspot sequence. Preferably the probe covers the full wild-type hotspot sequence and extends further a few nucleotides on each extremity (typically 1 to 10 nucleotides, notably 2 to 8, preferably 2 to 6, most preferably 2 to 5 or 2 to 4) to confer both its ability to bind properly and the resulting destabilization in case of mutation. In other words, the probe size is designed to confer its ability to bind properly to the wild-type hotspot sequence, while destabilizing hybridization of the HOTSPOT probes in the presence of at least one mutation in the hotspot sequence.

Preferably, according to the invention, the HOTSPOT probe covers a target sequence from the ligand binding domain (LBD) of the ESR1 gene (see Jeselsohn R et al., "*ESR1 mutations as a mechanism for acquired endocrine resistance in breast cancer*." Nature reviews Clinical oncology. 2015; 12(10):573-583). Most preferably, the HOTSPOT probe covers a target sequence that includes a least a known hotspot mutation sequence. Thus typically, a HOTSPOT probe according to the invention covers the full wild-type sequence of at least codons 536-538 of exon 8 from ESR1 and extends on each extremity as above defined. For example, as illustrated in the example a well-suited probe covers codons 536-540 and extends further on 1 nucleotide on 5' and 3' ends.

The REF probe is located in a non-variable region, which does not include the hotspot mutation sequence locus. The REF probe may partially overlap with the said hotspot sequence or be located outside of the said hotspot sequence. Preferably the second probe according to the invention is located outside of the said hotspot sequence. Thus in a preferred embodiment, the REF probe hybridizes with a wild-type sequence, which does not include codons 536-538 of exon 8. In ddPCR, the REF probe is used to quantify droplets with amplifiable DNA.

As per the drop-off assay of the invention, wild-type (WT) sequences will thus display a double positive fluorescence signal coming from the hybridization of both the REF and HOTSPOT probes, while droplets containing a mutated allele will present a shifted signal that results from the hybridization of the REF probe only.

The maximal fluorescence intensity signal associated with both the REF and HOTSPOT probes indicates the presence of a wild-type allele (i.e. a wild-type sequence in the target fragment).

As shown in the examples, the authors have shown that, not only the drop off assay of the present applicant allows to detect mutated ESR1 allele in exon 8, but also that the nature of the one or more mutation(s) can be further characterized based on the shift in the fluorescence intensity signal associated with the HOTSPOT probe with respect to the wild-type droplet cloud and/or the empty droplet cloud as a reference.

According to the present invention, amplification of the target DNA fragment occurs with a digital PCR technique. Typically, in such a technique, the PCR solution is divided in multiple compartments or droplets, which are made to run PCR individually.

Thermal cycling is performed to endpoint. Thus after multiple PCR amplification cycles (i.e. after completing PCR cycles), the raw PCR data are then collected by measuring the fluorescence signal associated with both the REF and HOTSPOT probes for each droplet.

The PCR data collection step is typically performed in an optical detector (for example the Bio-Rad QX-100 droplet reader can be used in ddPCR). Preferably at least a two-color detection system is used (for example to detect FAM and either HEX or VIC fluorescent labels). Droplets clouds can typically be established on 2D graphs by plotting the fluorescence level for each probe per droplet. In some embodiments, analysis may be achieved with appropriate software (such as the QuantaSoft v1.7.4 software for ddPCR or the ddPCR package on R cran.r-project.org/web/packages/ddpcr/index.html. Quantasoft allows manual assignment of the droplets to single REF positive or to the double REF/HOTSPOT positive population (i.e. or clouds).

Most preferably, the digital PCR reaction is designed to ensure that most droplets contain either 0 or 1 copy of targeted DNA fragment (notably depending on the quantity of DNA loaded in the reaction). It must be noted that due to biological variability that droplets classified in the single REF+ signal may include a residual (i.e., non-significant) MS signal. A threshold, under which a MS signal is considered as "a residual MS signal" can be determined by the one skilled in the art according to classical signal analysis techniques. Said threshold can be typically set using the R package that defines thresholds in an automatic way to avoid bias that might be introduced by manual assignment.

The number of droplets that are positive for the reference probe (REF probe) can be used to quantify the total number of target DNA fragments in the sample. The fraction of positive droplets can then be fitted to a Poisson distribution to determine the absolute initial copy number of the target DNA fragment in the input reaction mixture in units of copies/µl.

As indicated above, droplets containing WT target fragments (from wild-type alleles) display a maximal double positive fluorescence signal coming from the hybridization of both the REF and HOTSPOT probes (REF+/HOTSPOT+ droplets).

At the contrary, in droplets containing a mutated hotspot sequence in the amplified target DNA fragment (i.e. one or more mutation in the hotspot sequence), the non-hybridization (or low hybridization) of the HOTSPOT probe leads to a shift in the fluorescence intensity for the signal associated with the MS probe on the 2D graph, toward a single REF positive (REF+) population.

Typically mutant allele frequency can be determined as follow:

$$[(HOTSPOT_{low}/REF_+ droplets)/(HOTSPOT_{low}/REF_+ droplets)+(HOTSPOT_+/REF_+ droplets)]$$

The present inventors have demonstrated that the shift of the droplet cloud, with respect to the wild-type cloud depends on the nature of the one or more mutation(s) in the hotspot region from the target fragment.

Typically, once experimental conditions have been set (typically including the set of probes and primers as well as ddPCR conditions), the shift associated with each mutation can be determined in control conditions, using control sample including predetermined mutation or combination of mutations. Typically sample containing synthetic oligonucleotide with specific mutation or combination of mutations can be used for this purpose.

The results of the present invention provides the proof of principle that virtually all mutation from a selected hotspot region can be detected with the use of a single set of probe (including a HOTSPOT probe and a REF probe) as previously defined. Typically, any mutation comprised in the sequence covered by the HOTSPOT probe (i.e.: targeted sequence) will lead to a destabilization of the probe and will therefore induce a shift of the associated droplet cloud, with respect to the wild-type droplet cloud.

In particular, the results of the present application demonstrate that using a HOTSPOT probe as described, which covers a target sequence corresponding to codons 536-540 and includes the known hotspot mutation sequence of codons 536-538 allows to detect and/or characterize virtually all mutations in the targeted sequence. Thus the present invention allows the detection, discrimination and/or characterization of at least all known mutations at the consecutive amino acids L536, Y537 and D538 from exon 8 (see notably Weiyi Toy et al., "*Activating ESR1 Mutations Differentially Affect the Efficacy of ER Antagonists*", Cancer Discov 2017, (7) (3):277-287 and Chung J H et al., "*Hybrid*

*capture-based genomic profiling of circulating tumor DNA from patients with estrogen receptor-positive metastatic breast cancer*". Ann Oncol. 2017 Nov. 1; 28(11):2866-2873.), which includes with no limitation L536P, L536H, L536R, Y537N, Y537S, Y537C, Y537D, D538G and D538-L539ins and combinations thereof. In one embodiment, at least mutations selected from L536R, Y537S, Y537C, Y537N, D538G and combinations thereof (including the double mutation D538G/Y537C) can be detected and characterized according with the method of the invention. Notably the present invention also do detect and characterize more than 50%, more than 60% and typically at least 70% of the known mutations of the hotspot region including codons 536-538 of exon 8. Typically, the present invention allows to detect and characterize all the known mutation of said hotspot region from 8 that are present with a mutant frequency of more than about 2% (i.e.: L536H, L536P, Y537S, Y537C, Y537N and D538G).

Method for the Characterization of One or More Mutations of at Least Two Hotspot Mutation Sequences Combining a Drop-Off dPCR Assay and a Mutant-Specific dPCR In a preferred embodiment, the drop-off digital PCR assay of the invention as described above is further multiplexed with an unconventional mutation specific (MS) dPCR for identifying a mutation in a hotspot mutation sequence of a second target fragment from said DNA sample.

In such multiplexed embodiment, the PCR solution as previously defined further comprises:

a pair of primers suitable for amplifying said second target fragment of the DNA sample;

an oligonucleotide hydrolysis probe (MS-HOTSPOT), labeled with a (first) fluorophore, wherein said oligonucleotide MS-HOTSPOT probe is complementary to the hotspot mutation sequence of said second target fragment.

an oligonucleotide reference (MS-REF) hydrolysis probe, labeled with another/(a second) fluorophore, wherein MS-REF oligonucleotide probe is complementary to a wild-type (i.e.: invariable) sequence of said second target fragment located outside of the hotspot mutation sequence.

In this context, MS-REF probe is complementary to a wild-type sequence (i.e.: invariable), while the MS-HOTSPOT probe is specific for a given mutation. Thus in such mutant specific unconventional dPCR assay, droplets comprising mutant sequences will thus display a double positive fluorescence signal coming from the hybridization of both the REF and HOTSPOT probes, while droplets containing a wild-type allele will present a shifted signal that results from the hybridization of the REF probe only because the MS-HOTSPOT probe cannot hybridize onto WT sequences.

Typically said second target fragment is an ESR1 fragment. In a preferred embodiment, the second target fragment is located in the ligand-binding domain of ESR1 and includes a hotspot mutation sequence. Typically, said second target fragment includes exon 5 and notably the hotspot mutation region including codon 380. Thus typically the MS-HOTSPOT probe according to the invention covers a least a target sequence including a hotspot mutation sequence of the ligand-binding domain of ESR1. Most preferably, the MS-HOTSPOT probe covers a target sequence comprising codon 380 and is specific for a given mutation or combination of mutations.

When the second target fragment includes the hotspot mutation region corresponding to codon 380 of exon 5, the MS-HOSPOT probe is preferably specific for the E380Q mutation, as said mutation has been shown to be highly frequent. Thus in this embodiment, droplets comprising a mutant allele comprising mutation E380Q will display a double positive fluorescence signal from both MS-REFER-ENCE and MS-HOTSPOT probes, while droplets containing a wild-type sequence for exon 5 will display on single signal due to the hybridization of the REFERENCE probe only.

The inventors have shown that the present invention that combined a drop-off dPCR assay on exon 8 of ESR1 and a mutant specific assay for mutation E380Q allows to screen for mutations in exons 5 and 8 in a single reaction. In particular, the results of the inventors indeed provide evidence that each nucleotide change does not equally destabilize the complex "probe/target sequence", such that such the combined multiplex surprisingly allows detection, discrimination and/or characterization, of virtually all the most frequent ESR1 mutations that have been described so far, thus including with no limitation, mutations selected from L536P, L536H, L536R, Y537N, Y537S, Y537C, Y537D, D538G and D538-L539ins and combinations thereof (notably the double mutation D538GN537C) on exon 8 and mutation E380Q on exon 5.

The results also show that surprisingly both an excellent sensibility and a high specificity can be obtained with the combined test according to the invention, as it was notably demonstrated that ESR1 combined multiplex ddPCR performs better than standard targeted NGS (next generation sequencing) in identifying ESR1 mutation carriers, owing to its improved sensitivity.

General Characteristics of the Method of the Invention

Typically, digital PCR conditions can be designed as classically done in the field, for example regarding ddPCR as described in the Biorad's Guideline for ddPCR.

The method of the invention uses a primer/probe set as previously defined. Preferably, the primer pair is typically designed so as to have a $T_m$ lower than the $T_c$ of the reaction. The pair of primer can be designed using available computer programs.

Preferably primers are designed to generate amplicons of at least 80 base pairs (bp) notably at least 90 bp, or at least 100 bp. In some embodiments, primers are designed to generate amplicons under 150 bp, for compatibility with ctDNA detection.

Preferably also, probes and primers are designed such that the $T_m$ of the probes is greater than the $T_m$ of the primers.

Typically, the probes according to the invention are hydrolysis probes (also named TaqMan probes). Hydrolysis probes of the invention have a fluorophore covalently attached to their 5'-end of the oligonucleotide probe and a quencher.

Oligonucleotide probes are detectably labeled with a fluorescent label which can be selected, for example, from the group consisting of FAM (5- or 6-carboxyfluorescein), VIC, NED, Fluorescein, FITC, IRD-700/800, CY3, CY5, CY3.5, CY5.5, HEX, TET (5-tetrachloro-fluorescein), TAMRA, JOE, ROX, BODIPY TMR, Oregon Green, Rhodamine Green, Rhodamine Red, Texas Red, Yakima Yellow, Alexa Fluor PET, Biosearch Blue™, Marina Blue®, Bothell Blue®, Alexa Fluor®, 350 FAM™, SYBR® Green 1, Fluorescein, EvaGreen™, Alexa Fluor® 488 JOE™, 25 VIC™, HEX™, TET™, CAL Fluor® Gold 540, Yakima Yellow®, ROX™, CAL Fluor® Red 610, Cy3.5™, Texas Red®, Alexa Fluor® 568 Cry5™, Quasar™ 670, LightCycler Red640®, Alexa Fluor 633 Quasar™ 705, LightCycler Red705®, Alexa Fluor® 680, SYTO®9, LC Green®, LC Green® Plus+, and EvaGreen™. Preferably, the detectable label is selected from 6-carboxyfluorescein, FAM, or tetra-chlorofluorescein, (acronym: TET), Texas Red, Cyanin 5, Cyanine 3, or VIC™.

It is noted that while the fluorophores associated respectively with the REF probe and the HOTSPOT probe on one side and with the MS-REF probe and the MS-HOTSPOT probes on the other side should be different, in one embodiment, the fluorophores of the both reference probes (i.e.: REF and MS-REF) and the both hotspot probes (i.e.: HOT-SPOT and MS-HOTSPOT) can be the same or different. Selection of adapted fluorophores is classical in the field can be typically achieved according to general ddPCR recommendations. As a matter of example, well-suited fluorophores include FAM and VIC as used in the experimental results.

The quencher may be an internal quencher or a quencher located in the 3' end of the probe. Typical quenchers are tetramethylrhodamine, TAMRA, Black Hole Quencher or nonfluorescent quencher. Hydrolysis probes usable according to the invention are well-known in the field www.sig-maaldrich.com/technical-documents/articles/biology/quan-titative-pcr-and-digital-pcr-detection-methods.html). The quencher molecule quenches the fluorescence emitted by the fluorophore when excited by the cycler's light source typically via FRET (Forster Resonance Energy Transfer). As long as the fluorophore and the quencher are in proximity, quenching inhibits any fluorescence signals. Such probes are designed such that they anneal within the target region amplified by a specific set of primers. As the Taq polymerase extends the primer and synthesizes the nascent strand, the 5'-3' exonuclease activity inherent in the Taq DNA polymerase then separates the 5' reporter from the 3' quencher, which provides a fluorescent signal that is proportional to the amplicon yield.

The reference and hotspot probes according to the invention are located within the same amplicon. The probes are designed according to the well-established practice in the art to preferably minimize PCR artifact and to specifically hybridize with the sequences as defined below. As mentioned above for each set of probe (reference/hotspot) the reference and the hotspot probes are labeled with distinct fluorophores in order to allow separate detection of their respective signal.

In some embodiments, the hydrolysis probes according to the invention may include a minor groove binder (MGB) moiety at their 3' end. Such MGB typically increases the melting temperature (Tm) of the probe and stabilizes probe-target hybrids. The oligonucleotide probes have a nucleotide sequence length of about 10 to about 50 nucleotides. Preferably, the oligonucleotide probes (and in particular the MS probe) have a nucleotide sequence length of at least 20 nucleotides, notably about 20 to 40, or 30 to 50 or notably 30 to 40 nucleotides.

As used herein, the term "sample" refers to anything which may contain DNA and notably the DNA fragment to be amplified. In some embodiment, the "sample" contains RNA and is therefore submitted to a reverse transcription step. The sample may be a biological sample, such as a biological fluid or a biological tissue. Examples of biological fluids include urine, blood, plasma, serum, saliva, semen, stool, sputum, cerebrospinal fluid, tears, mucus, pancreatic juice, gastric juice amniotic fluid, serous fluids such as pericardial fluid, pleural fluid or peritoneal fluid.

Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumor tissue, lymph nodes, arteries and disseminated cell(s). The tissue can be fresh, freshly frozen, or fixed, such as formalin-fixed paraffin-embedded (FFPE) tissues. The sample can be obtained by any means, for example via a surgical procedure, such as a biopsy, or by a less invasive method, including, but not limited to, abrasion or fine needle aspiration. Preferably, the DNA sample is selected from the group consisting of: tumor tissue, disseminated cells, feces, blood cells, blood plasma, serum, lymph nodes, urine, saliva, semen, stool, sputum, cerebrospinal fluid, tears, mucus, pancreatic juice, gastric juice, amniotic fluid, cerebrospinal fluid, serous fluids such as pericardial fluid, pleural fluid or peritoneal fluid.

The DNA and notably the target DNA fragment can be genomic DNA or DNA issued from reverse transcriptase. The genomic DNA can be constitutional DNA, tumor DNA or fetal DNA. In some embodiments, notably when the sample is a biological fluid, the DNA sample may contain cell-free DNA (cfDNA), or circulating DNA. Early studies have shown that tumor DNA is released into the circulation, and is present in particularly high concentrations in plasma and serum in a number of different types of cancers (Leon et al., 1977 Cancer Res 37:646-650; Stroun et al., 1989 Oncology 46:318-322). Thus, DNA sample according to the invention can contain cell-free tumor DNA (cfDNA) or circulating tumor DNA (ctDNA). In another embodiment, the DNA sample contains cell-free fetal DNA. Due to its high sensitivity, the method of the invention is particularly well-suited to be used on plasma sample containing low concentration of circulating, or cell-free target DNA such as cell-free or circulating tumor DNA or fetal DNA. In some embodiments of the present invention, the DNA can be obtained from reverse transcription of an RNA sample.

Typically a DNA sample according to the invention is obtained from a subject. The subject, or the patient (both terms can be used interchangeably) of the invention is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

In some embodiments of the invention, the subject is suffering from a cancer, is in remission of a cancer, is under cancer treatment, or is at risk of suffering from a cancer notably based on family history. In some embodiments for example the subject has familial tumor predisposition.

The cancer may be a solid cancer or a "liquid tumor" such as cancers affecting the blood, bone marrow and lymphoid system, also known as tumors of the hematopoietic and lymphoid tissues, which notably include leukemia and lymphoma. Liquid tumors include for example acute myelogenous leukemia (AML), chronic myelogenous leukemia (CML), acute lymphocytic leukemia (ALL), and chronic lymphocytic leukemia (CLL), (including various lymphomas such as mantle cell lymphoma or non-Hodgkins lymphoma (NHL).

Solid cancers notably include cancers affecting one of the organs selected from the group consisting of colon, rectum, skin, endometrium, lung (including non-small cell lung carcinoma), uterus, bones (such as Osteosarcoma, Chondrosarcomas, Ewing's sarcoma, Fibrosarcomas, Giant cell tumors, Adamantinomas, and Chordomas), liver, kidney, esophagus, stomach, bladder, pancreas, cervix, brain (such as Meningiomas, so Glioblastomas, Lower-Grade Astrocytomas, Oligodendrocytomas, Pituitary Tumors, Schwannomas, and Metastatic brain cancers), ovary, breast, head (brain) and neck region, testis, prostate and the thyroid gland.

Preferably according to the invention the cancer is a breast cancer, including primary and advanced breast cancer, notably metastatic breast cancer. Typically the cancer can be an advanced breast cancer, notably an ER-positive breast cancer developed after the development of acquired secondary resistance to aromatase inhibitors.

Clinical Applications: Diagnosis and Prognosis Methods, Therapeutic Treatment and Patient Monitoring.

The method for identifying and/or characterizing mutations in at least one hotspot mutation sequence in a target DNA fragment as described above has several major and direct clinical applications.

As previously mentioned the present invention now provides a method, which is both simple to design and involves reduces costs, as compared to the known methods in the field. Furthermore the method of the invention can easily be achieved on small size sample and is both highly specific and sensitive even for the detection of circulating tumor DNA.

The results included herein also demonstrate that the combined multiplex ESR1 assay presently disclosed allows detection of polyclonal alterations with high sensibility and specificity. Thus the method of the invention can be used for detection and monitoring of patients carrying polyclonal mutations.

The present invention also includes an in vitro method for the monitoring of mutation(s) from a DNA sample of a patient, or for the prognosis of cancer in said patient. In such embodiments, the method for identifying and discriminating or characterizing mutations as described above can be performed at various time points in a patient at risk of having a cancer (typically due to familial predisposition), or in a patient suffering from a cancer at various time points of the disease. The method as herein described thus allows to identify and monitor the evolution of the one or more mutation(s) during the time course of the disease, and/or during or after the treatment.

In this context, the method is thus particularly well-suited for the monitoring of ESR1 mutation(s) and for the prognosis of cancer in a patient suffering from breast cancer, notably patients which are treated with aromatase inhibitors. The method as described above may be thus performed at various time points of the disease, such as before treatment with aromatase inhibitors, during the treatment and after the treatment.

Indeed, as mentioned previously, it is clearly established that ESR1 mutations, while rarely detected in primary tumors and at first metastatic relapse, increase alongside the exposure of patients to aromatase inhibitors in ER-positive HER2-negative metastatic breast cancer patients. Such method therefore advantageously allows monitoring the appearance, progression or reappearance of the disease. In particular, the method may allow monitoring the development of an advanced breast cancer with secondary resistance to aromatase inhibitors. Notably the present invention allows monitoring evolution of mutant sub-clones that may appear/or disappear during the time course of the disease, notably during treatment with aromatase inhibitors (Als) or even in remission periods.

Alternatively, the discrimination and notably, the detection and/or characterization of ESR1 mutation may also allow establishing a prognosis for a patient suffering from breast cancer, as the detection of ESR1 mutations have been classically associated with worst survival prognosis.

Typically, in a method for the prognosis of cancer, notably breast cancer, the target DNA fragment is originating from a tumor. In such embodiment, the DNA may classically be circulating tumor DNA obtained from a serum sample.

The present invention also includes an in vitro method for predicting the efficacy of an endocrine therapy for breast cancer in a subject suffering from a cancer, wherein the method for identifying and/or characterizing mutations in at least one hotspot mutation sequence in a target DNA fragment as described above is performed on a DNA sample from a patient during the time course of the treatment. In such embodiment, the target DNA fragment is also originating from a tumor.

Such method would advantageously predict that second-line Aromatase inhibitors would not help if ESR1 mutations are present, whereas an antiestrogen might. Early characterization of ESR1 mutations might thus allow for cessation of ineffective endocrine therapies and switching to other treatments, before the emergence of metastatic disease. Furthermore characterization of specific ESR1 mutation may also allow to precisely adapt the treatment. Indeed, it has been shown that differential sensitivity of ESR1 mutant, notably in the ligand-binding domain (NBD) including exon 8, to selective estrogen receptor degraders (ERD). Toy et al. (Cancer Discovery March 2017; DOI:10.1158/2159-8290.CD-15-1523) showed that among the mutants, Y537S was the most constitutively active and required the highest drug concentration to fully inhibit the receptor. This specific mutant proved to be less effectively antagonized in vivo by fulvestrant compared with more potent and orally bioavailable SERD AZD9496. Thus collectively, these data suggest that activating ESR1 LBD mutations differentially affect the efficacy of ER antagonists. The present invention is therefore highly relevant as it allows following the evolution of ESR1 mutant sub-clone(s) and potentially fine tuning of the treatment from potentially a simple blood test. Such method is also well-suited for large scale screening in a public health point of view.

Typically, the present method and in particular the combined multiplex assay can be used for predicting the patient response to estrogen receptor down-regulators, such as, for example, palbociclib-fulvestrant therapy.

The improved analytical sensitivity of the ESR1-ddPCR assay (more particularly the combined multiplex assay), as herein disclosed, is particularly useful to monitor ctDNA during breast cancer treatment follow-up or monitoring. The inventors indeed demonstrated that ESR1 mutations are good markers for ctDNA dynamics exploration and prediction of treatment response. In other words, assessment of ctDNA copy levels through detection of ESR1 mutant copy levels using the ddPCR assay as per the present disclosure (in particular the combined multiplex assay) can be used for estimating disease progression and patient survival (e.g.: progression free survival). Thus the present disclosure also encompasses the use of ESR1 copy level as a biomarker for disease progression and patient survival, wherein the ESR1 copy level is assessed according to the method as herein disclosed.

The present invention thus also encompasses an in vitro method for the monitoring of mutation(s) from a DNA sample of a patient, or for the prognosis of cancer in said patient (notably for assessment of patient survival) comprising detection of the ctDNA copy level in a patient sample, wherein the ctDNA copy level is assessed by detection of the ESR1 mutant copy level, using the ddPCR assay as herein disclosed (notably the combined multiplex ddPCR assay).

The present invention also relates to a method of treatment of a breast cancer in a subject in need thereof comprising:

a) performing the method for detecting and/or characterizing a mutation on a ESR1 DNA target fragment, from a DNA sample from a subject during the time course of the treatment, and b) adapting the endocrine therapy as a function of the specific ESR1 mutation(s) which has/have been identified at step a);

wherein the target fragment is originating from a tumor.

Typically as mentioned above the treatment may be adapted to avoid aromatase inhibitors if case of appearance of at least one ESR1 mutation or to adapt the treatment to a specific ER antagonist or with efficient concentration, as function of the specific mutation(s) which has been characterized.

Kits:

The present invention also encompasses a kit for qualitative investigation of ESR1 hotspot mutations in a target fragment from a DNA sample:

a pair of primers suitable for amplifying an ESR1 target fragment (including the hotspot mutation sequence);

an oligonucleotide reference (REF) hydrolysis probe, labeled with a fluorophore, wherein said REF oligonucleotide probe is complementary to a wild-type sequence of the target fragment located outside of the hotspot mutation sequence;

an oligonucleotide hotspot (HOTSPOT) hydrolysis probe, labeled with another fluorophore, wherein said oligonucleotide HOTSPOT probe is complementary to a wild-type sequence of the hotspot mutation sequence of the target DNA fragment, and a thermostable DNA polymerase.

In one embodiment, the kit defined above further comprises:

a pair of primers suitable for amplifying said second ESR1 target fragment of the DNA sample;

an oligonucleotide hydrolysis probe (MS-MUT), labeled with a fluorophore, wherein said oligonucleotide MUT probe is complementary to the hotspot mutation sequence of said second target fragment.

an oligonucleotide reference (MS-REF) hydrolysis probe, labeled with another fluorophore, wherein MS-REF oligonucleotide probe is complementary to a wild-type sequence of said second target fragment located outside of the hotspot mutation sequence.

Primers, probes, ESR1 target fragment and hotspot mutation sequence usable in a kit according to the invention have been previously described.

Thermostable DNA polymerases are typically described in Newton and Graham 1994 In: PCR, BIOS Scientific Publishers, Ltd., Oxford, UK. 13. Advantageously, the thermostable polymerase is the Taq polymerase.

The kit as above mentioned can be used in the clinical applications as previously described.

FIGURES LEGENDS

FIG. 1: ESR1 exons 5 and 8 assay design. A. Assay to detect the E380Q mutation in exon 5: wild-type alleles generate a signal from the reference probe only (VIC+, green cloud) whereas E380Q alleles generate a double positive signal (VIC+/FAM+, blue cloud). B. The Drop-off Ex8 assay detects the clustered hotspot mutations located in exon 8 (D538G in this example). Wild-type alleles generate a signal from both the reference and drop-off probes (FAM+/

VIC+, green cloud) whereas alleles with alterations in codons 536-538 generate a signal from the reference probe only (FAM+, blue cloud). C. The multiplex assay detects, in a single reaction, the E380Q mutation (left panel) and mutations in exon 8 (right panel, D538G in this example). Cloud #1=Empty droplets; Cloud #2=WT Ex5; Cloud #3=WT Ex8; Cloud #4=E380Q (left panel) or MUT Ex8 (right panel); Cloud #5=WT Ex5+WT Ex8; Cloud #6=E380Q+WT Ex5+WT Ex8.

Figure 2:
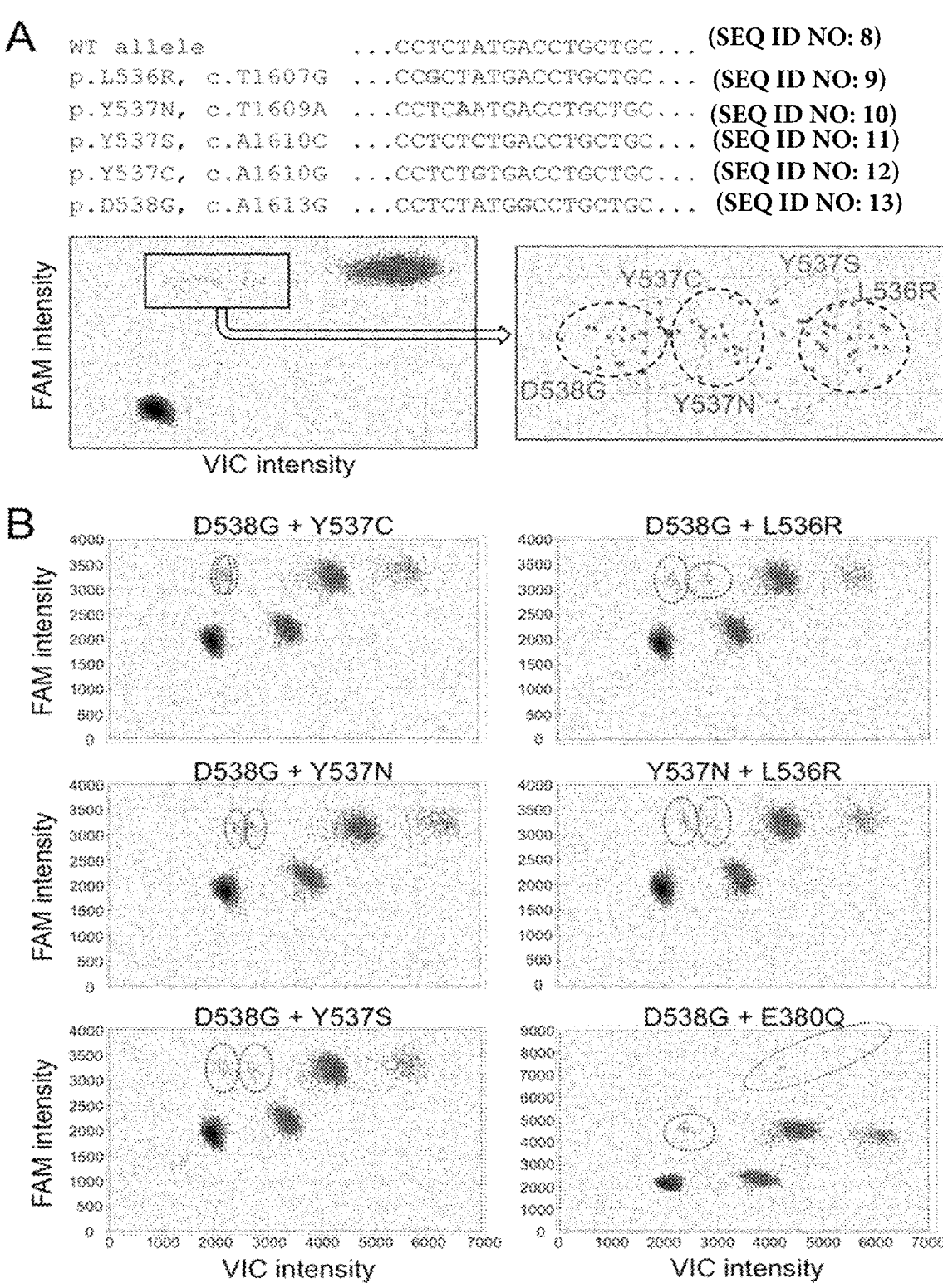

FIG. 2: Detection of ESR1 polyclonal mutations. A. Wild-type ESR1 exon 8 (SEQ ID NO: 8) and most frequent mutations located in ESR1 exon 8 targeted by the Drop-off Ex8 assay (SEQ ID NO: 9 to 13). B. Representative examples of double mutations (synthetic oligonucleotides combined) detected in multiplex condition. FAM and VIC intensities are shown in arbitrary units.

Figure 3:
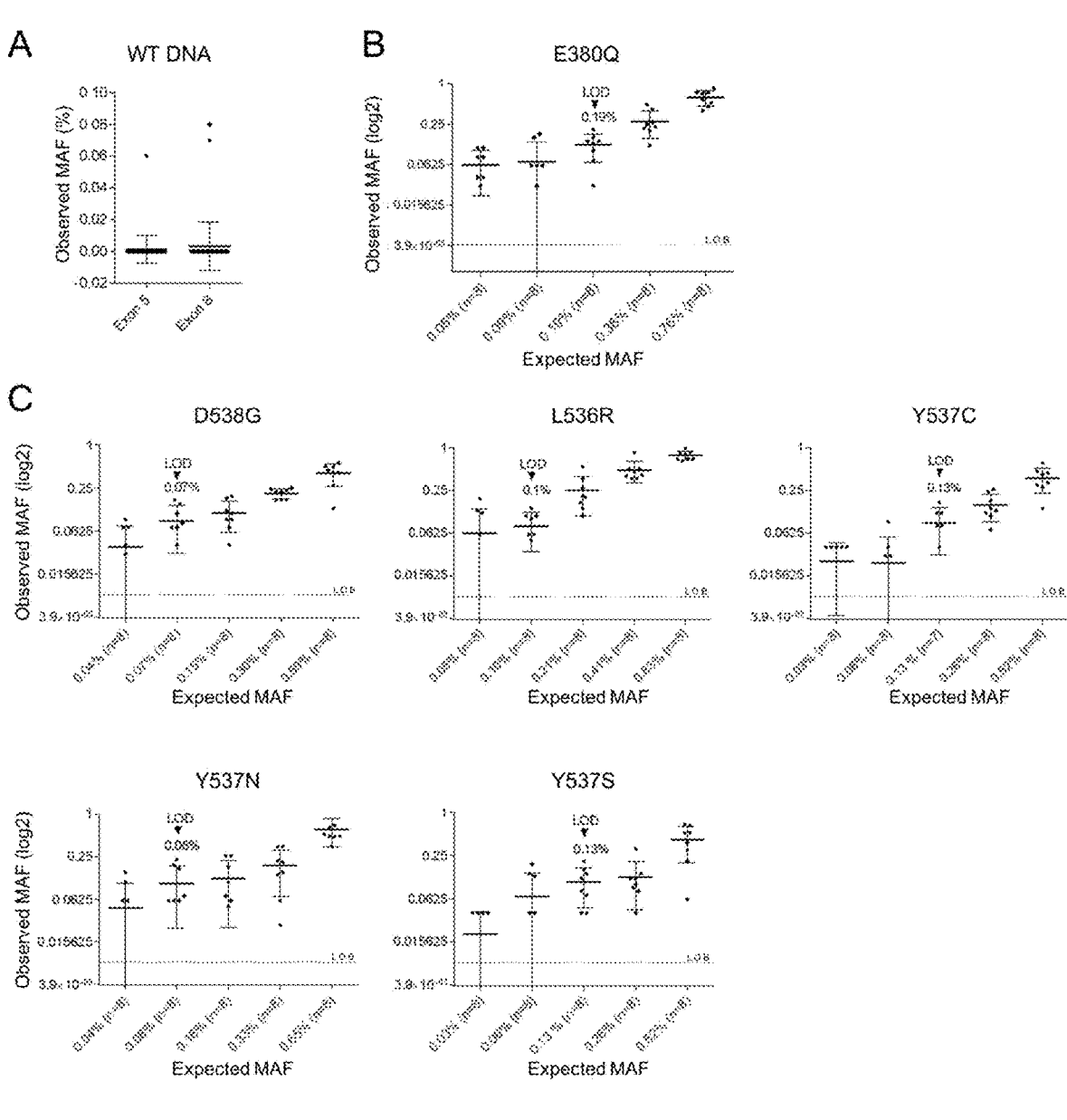

FIG. 3: In vitro performance of the multiplex ESR1-ddPCR. A. False positive events for exons 5 or 8 mutations observed from pure WT DNA tested with the multiplex ESR1-ddPCR. B. LOD estimation for exon 5 E380Q mutation. C. LOD estimation for exon 8 mutations D538G, L536R, Y537C, Y537N or Y537S. See method section for more details. LOB: limit of blank, LOD: limit of detection, estimated as the 95% CI of the mean false-positive calls.

Figure 4:
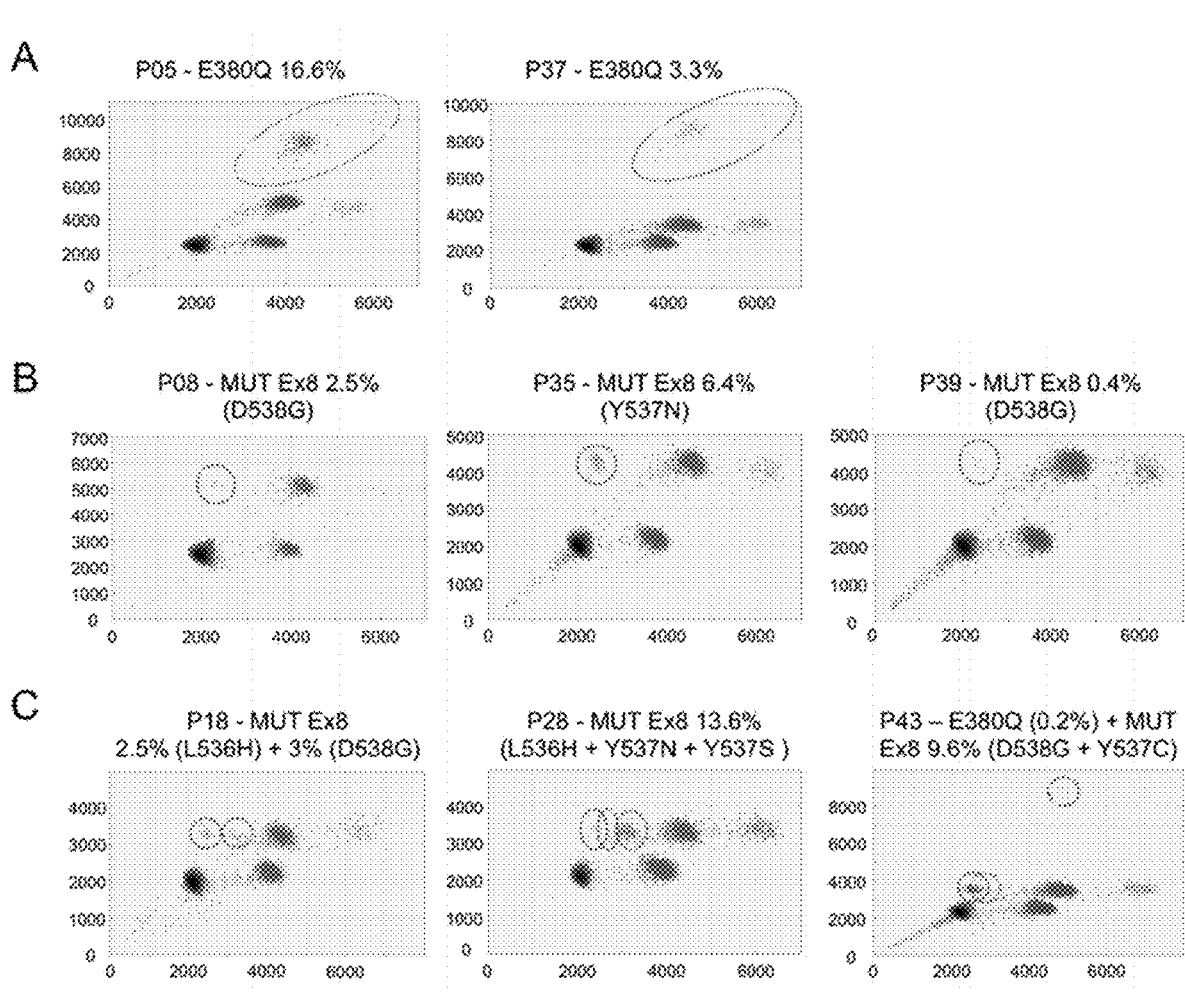

FIG. 4: Validation of the ESR1 ddPCR multiplex assay on patient plasma samples. Representative ddPCR profiles for E380Q mutation (A), exon 8 mutations (D538G or Y357N) (B) and polyclonal ESR1 mutations (C). Case P-18, double exon 8 mutations identified as L536H and D538G; case P-28, exon 8 mutations identified as L536H, Y537N and Y537S and case P-43, exon 5+exon 8 mutations identified as D538G, Y537C and E380Q by NGS. FAM and VIC intensities are shown in arbitrary units. MAFs determined by ddPCR are indicated above each plot together with the mutation identified by NGS in brackets.

Figure 5:
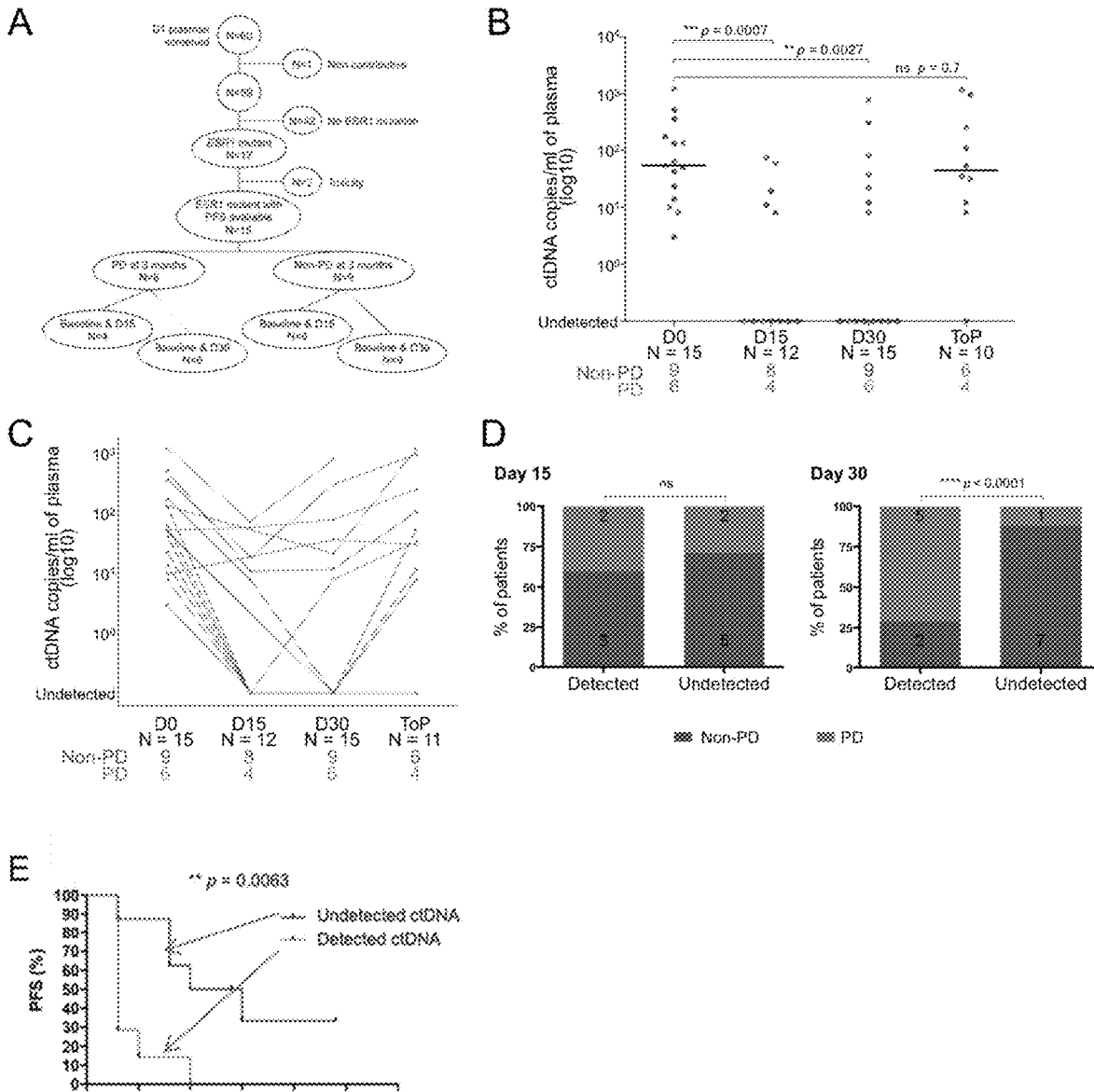

FIG. 5: Monitoring of circulating ESR1 mutant copies to predict response to palbociclib-fulvestrant therapy A. Flow chart of plasma samples analyzed from the ALCINA cohort 6 'Palbociclib' (NCT02866149) for ESR1 mutations with the ESR1-ddPCR multiplex. PD: progressive disease, Non-PD: regressive or stable disease. B. Number of ctDNA copies detected per ml of plasma collected at the 4 time points during treatment follow-up (D0, N=15; D15, N=12; D30, N=15; ToP, N=10). C. ctDNA dynamics observed during treatment follow-up in patients experiencing progressive disease (PD, red) versus regressive or stable disease (non-PD, green) at 3 months according to RECIST criteria. (D0: non-PD=9, PD=6; D15: non-PD=8, PD=4; D30: non-PD=9, PD=6; ToP: non-PD=6, PD=4). D. Two sample test proportions for detectable and undetectable ctDNA distribution at D15 and D30. E. Survival (PFS) according to ctDNA detection at D30 (E).

EXAMPLES

Material and Methods
Droplet Digital PCR Assay
TaqMan® Probes and Primer Design

For the E380Q mutation in exon 5, the assay used a probe specifically targeting the E380Q mutation (E380Q probe, FAM-labeled) and a reference probe (REFex5 probe, VIC-labeled) annealing to an adjacent invariant region (FIG. 1A). For the clustered hotspot mutations in exon 8, a drop-off assay was designed using a probe targeting the WT sequence of codons 536, 537 and 538 where mutations are likely to be found (Hotspot probe, VIC-labeled) and a reference probe (REFex8 probe, FAM-labeled) annealing to an adjacent invariant region (FIG. 1B). For compatibility with ctDNA detection, primers were designed to generate amplicons under 150 bp (101 bp and 125 bp for exons 5 and 8, respectively). The following primers were used to amplify (a) exon 5: Fwd primer: 5'-TTGCTTGTTTTC-AGGCTTTGTGGA-3' (SEQ ID NO: 1); Rev primer 5'-AGCGCCAGACGAGACCAATCAT-3'(SEQ ID NO: 2); and (b) exon 8: Fwd primer: 5'-ACAGCAT-GAAGTGCAAGAACGT-3' (SEQ ID NO: 3); Rev primer 5'-TGGCTTTGGTCCGTCTCCTC-3' (SEQ ID NO: 4). The following TaqMan probes (Life Technologies) with a 5' fluorophore and a 3' non-fluorescent quencher (NFQ) were designed as follows: REFex5 5'-(VIC)-TGACCCTCCAT-GATC-(MGB NFQ)-3' (SEQ ID NO: 5); E380Q 5'-(6-FAM)-ACCTTCTACAATGTGCCTG-(MGB NFQ)-3' (SEQ ID NO: 6); REFex8 5'-(6-FAM)-CTAGCCGTG-GAGGGGC-(MGB NFQ)-3' (SEQ ID NO: 7); Hotspot 5'-(VIC)-CCTCTATGACCTGCTGC-(MGB NFQ)-3' (SEQ ID NO: 8).
ddPCR Mix Preparation ddPCR reactions were performed in 20 μL according to the manufacturer's protocol. Briefly, 20 μL mastermix solution containing ddPCR™ Supermix for probes without dUTP (Bio-Rad Laboratories) at a final concentration of 1×, relevant primers at 450 nM each and relevant TaqMan® probes (E380Q+REFex5 or Hotspot+REFex8 in simplex conditions or both assays combined in multiplex conditions) at 250 nM each (Applied Biosystems), DNA template (up to 8 μL) and nuclease-free water were loaded into a disposable droplet generator cassette (Bio-Rad). After adding 70 μL of droplet generation oil (Bio-Rad), the cassette was loaded into a QX100 Droplet Generator (Bio-Rad). Generated droplets were transferred to a 96-well PCR plate and PCR reactions were run on a C1000 thermal cycler (Bio-Rad) under the following program: 95° C. 10 min, 40 cycles of (94° C. 30 sec, 58° C. 60 sec), 98° C. 10 min. For optimization experiments, we used 20 ng (6,060 genome equivalent) of DNA per reaction. For the mutation screening in patient samples, we used 8 μL of cell-free DNA (cfDNA). Negative controls with no DNA and positive controls (E380Q and D538G mutations) with 6,060 WT genome-equivalent from peripheral blood mononucleated cells (PBMC) were included at each run. Reactions were analyzed on the Bio-Rad QX100 droplet reader.
ddPCR Data Analysis The concentration of mutant DNA copies was estimated using the dedicated workflow available in the QuantaSoft v1.7.4 software. For the E380Q mutation, the number of mutant copies per droplet is equivalent to the number of $VIC^+/FAM^+$ droplets in simplex conditions and to clouds #4 and #6 in multiplex conditions (FIG. 1). The mutant allele frequency (MAF) was calculated as follows: ($VIC^+/FAM^+$ droplets/($VIC^+/FAM^+$ droplets+$VIC^+/FAM^-$ droplets)) for simplex conditions and (clouds #4+#6/(clouds #4+#6+#2+ #5)) for multiplex conditions. For mutations in exon 8, the number of mutant copies per droplet is equivalent to the number of $VIC^{low}/FAM^+$ droplets in simplex conditions and to cloud #4 in multiplex conditions. The MAF was calculated as follows: ($VIC^{low}/FAM^+$ droplets/($VIC^{low}/FAM^+$ droplets+$VIC^+/FAM^+$ droplets)) for simplex conditions and (cloud #4/(clouds #4+#3+#5)) for multiplex conditions. Samples were run in triplicates and were considered to be positive if the merged replicates presented a minimum of 3 mutant droplets for E380Q or 8 mutant droplets for exon 8 and if the average MAF was higher than the defined LOD of the multiplex assay.

In Vitro Performance

The limit of blank (LOB) was determined as previously reported (13,15,17,18). Briefly, we defined the false-positive mean and associated standard deviation (SD) of the E380Q and Drop-off Ex8 assays, in simplex or multiplex conditions by analyzing 48 replicates of WT genomic DNA extracted from PBMC. Then, the calculated 95% confidence interval was used to define the LOB. To assess the limit of detection (LOD) of the E380Q and Drop-off Ex8 assays, we used synthetic oligonucleotides harboring E380Q, or the most frequent mutations in exon 8 (L536R, Y537C, Y537N, Y537S or D538G). Serial dilutions in 10 ng (3,030 genome equivalent) of WT DNA from PBMC, reproducing MAFs from 0.8% to 0.04%, were analyzed in 8 replicates for each mutated oligonucleotide.

Validation in Clinical Samples

All plasma samples analyzed for ESR1 mutation status were collected from patients with AI-resistant ER+ HER2− MBC. Patients were prospectively enrolled at the Institut Curie (Paris, France) in the ethically-approved ALCINA study (NCT02866149, cohort 6) after signed informed consent and that were included prior to the initiation of a new line of therapy with palbociclib and fulvestrant. Progression-free survival (PFS), defined as the time from inclusion in the study to progression disease (PD) or death from any cause, was collected prospectively. Survival analysis was performed using Kaplan-Meier plots with significance tested using the log-rank test. Plasma was isolated from fresh blood collected in EDTA blood collection tubes (BD Vacutainer®) within 3 hours as previously performed in the laboratory (19,20) and stored at −80° C. until needed. For ESR1 screening, 2 mL of plasma were thawed and cfDNA extracted using the QIAamp® Circulating Nucleic Acid Kit (Qiagen) according to the manufacturer's protocol. cfDNA was quantified with Qubit (Life Technologies) and stored at −20° C. until use. In parallel to ddPCR experiments, targeted-NGS on a panel of 39 cancer-related genes was performed in a blind fashion to allow head-to-head comparison with the ESR1-ddPCR assay. Following library preparation, samples were subjected to ultra-deep sequencing on Illumina HiSeq2500 using a 2×100 bp paired-end configuration. Read depth obtained for the two ESR1 hotspots regions was higher than 5800×. Paired-end read alignments were performed on GRCh37 (hg19) human reference with Bowtie2 (v2.1.0). Once aligned, paired-end reads that map to multiple locations or with poor mapping quality (score<6) were removed. Pileup files were generated using samtools (v.1.1) and variant calling was performed using Varscan2 (v.2.3.6). A minimum base quality of 15 was required to count for a read at a position, and only variants supported by a minimum of 5 mutated reads at a position with a minimum read depth of 12 were selected. Additionally, the nucleotide composition for each position of the regions containing the two ESR1 hotspots was extracted from the BAM alignment files using GATK (v.3.5).

Results

Screening of Multiple ESR1 Hotspot Mutations by ddPCR

Based on the evidence that more than 80% of the activating ESR1 mutations found in ER+ HER2− MBC patients resistant to AI alters codon 380 in exon 5 and the codons 536, 537 and 538 in exon 8 (19% and 64% respectively), we developed a ddPCR assay targeting these two regions. This assay is composed of only two pairs of TaqMan probes, which can be combined in a single ddPCR reaction. The first pair targets specifically the E380Q mutation in exon 5, using a probe complementary to the E380Q mutant allele (E380Q probe, FAM-labeled) and a reference probe spanning an adjacent invariable region (REFex5 probe, VIC-labeled) (FIG. 1A, left panel). In this unconventional E380Q assay, droplets containing WT alleles are VIC-positive only, because the E380Q probe cannot hybridize onto WT sequences, whereas droplets containing E380Q mutant alleles are double positive (VIC⁺/FAM⁺) (FIG. 1A, right panel). The second pair of probes, constituting the Drop-off Ex8 assay, targets the clustered mutations in exon 8 using a probe complementary to the WT sequence of the altered region (Hotspot probe, VIC-labeled), which detects all the mutations occurring at codons 536, 537 and 538, together with a reference probe spanning an invariable region within the same amplicon (REFex8 probe, FAM-labeled) (FIG. 1B, left panel). Therefore, droplets containing WT alleles are double positive (FAM⁺/VIC⁺) whereas the mismatch induced by the mutations leads to a VIC signal decrease (FAM⁺/VIC^{low}), resulting in a shift of the droplet cloud (MUT Ex8) toward a single FAM-positive population (FIG. 1B, right panel).

The multiplexed assay, combining primers and probes from the E380Q and the Drop-off Ex8 assays, allows to screen for mutations in exons 5 and 8 in a single reaction. In a test using synthetic E380Q or D538G oligonucleotides, we could distinguish each WT and mutant clouds for exons 5 and 8 in multiplex conditions (FIG. 10). We observed an additional cloud of droplets containing both WT Ex5 and WT Ex8 amplicons (FIG. 10, Cloud #5), which we also find in WT samples (data not shown), as well as a cloud containing E380Q and WT copies when testing for the E380Q mutation (FIG. 10, left panel, Cloud #6), and not observed when testing for the D538G mutation.

Detection of Polyclonal Alterations

In addition to the D538G mutation, we tested four other synthetic oligonucleotides harboring the Y537C, Y537N, Y537C or L536R mutations found in exon 8. We observed that the position of the MUT Ex8 cloud was dependent on the mutation tested (FIG. 2A). This suggests that each nucleotide change does not equally destabilize the complex 'probe/target sequence'. The largest shifts were observed for the mutations D538G and Y537C. Both clouds of droplets containing these mutant alleles were localized in the same area and were therefore indistinguishable from each other; whereas the clouds for Y537N, Y537S and L536R displayed smaller shifts and were distinct from the D538G/Y5370 cloud. We further tested combinations of two mutant oligo-nucleotides in multiplex conditions confirming that multiple mutations in exon 8 (e.g., D538G+Y537N, D538G+Y537S, D538G+L536R or Y357N+L536R) display a specific pattern (FIG. 2B). We clearly detected the combination of one mutation in exon 8 (e.g., D538G) with E380Q (FIG. 2B). The multiplex ESR1-ddPCR can thus identify patients carrying polyclonal alterations, as previously reported (8, 9).

In Vitro Performances

We further estimated the specificity and sensitivity of the ESR1-ddPCR by analyzing 48 replicates of pure WT DNA and serial dilutions of the mutant synthetic oligonucleotides recapitulating MAFs from 0.8% to 0.04% (see Methods section for more details). The ESR1-ddPCR assay showed high specificity with a maximum of one false-positive event observed per reaction (FIG. 3A). The limit of blank (LOB) was estimated at 0.004% for exon 5 mutations and 0.008% for exon 8 mutations. The limit of detection (LOD), defined as the lowest MAF with all replicates presenting values above the LOB, was estimated at 0.19% in mutant allele frequency for E380Q (FIG. 3B) and ranged from 0.07 to 0.13% depending on the exon 8 mutation tested (FIG. 3C). LOB and LOD were also tested in simplex conditions and similar values were observed (LOB were 0.01% for the Drop-off Ex8 assay and 0.003% for the E380Q assay; LOD were 0.09% for mutation E380Q and ranging from 0.06 to 0.1% depending on the exon 8 mutation tested).

Validation in Clinical Samples

To validate the performance of the ESR1 multiplex ddPCR assay, we tested a series of 43 plasma samples from a prospective cohort of patients with HR+ HER2− MBC progressing under hormone therapy. We successfully detected ESR1 mutations in 11 out of the 42 (26%) informative patient samples (Table 1). Four cases (P-05, P-17, P-37 and P-43) harbored an E380Q mutation (36% of the mutant cases, FIG. 4A) and 8 cases (P-08, P-18, P-20, P-25, P-28, P35, P-39 and P-43) carried at least one mutation in exon 8 (73% of the mutant cases, FIG. 4B). Interestingly, based on the shape and the location of the MUT Ex8 clouds, we detected that samples P-18 and P-28 harbored multiple mutations (FIG. 4C). We also observed that P-43 harbors ESR1 mutations in both exons 5 and 8 (FIG. 4C). In parallel, targeted-NGS, including the ESR1 gene, has been performed on 32 plasma samples, for which we had sufficient cfDNA, to allow head-to-head comparison with the ESR1-ddPCR assay. Importantly, NGS analysis was performed in a blinded fashion, with no prior knowledge of ddPCR results. The samples sequenced included 10 mutant and 22 WT cases according to ddPCR analysis. All ESR1 mutations detected by ddPCR were confirmed by NGS except for 2 cases (P-17 and P-20), in which the ESR1 MAF was found to be <1% by ddPCR. P-25 was not tested with NGS due to lack of cfDNA. We also confirmed the WT status of the 22 remaining plasma samples. In case P-18, NGS results indicated that the mutations were D538G and L536H, a combination we did not test before. In case P-28, we observed 3 mutations in exon 8: L536H, Y537N and Y537S. Interestingly, for case P-35, NGS showed that the mutation in exon 8 was Y537N, which did not result from the usual C>T substitution in position 1609, but from a small deletion/insertion at nucleotides 1608-1609 (1608_1609 delinsTA). Overall, the ESR1 multiplex ddPCR performs better than standard targeted NGS in identifying ESR1 mutation carriers owing to its improved sensitivity.

Monitoring of Circulating ESR1 Mutant Copies to Predict Response to Palbociclib-Fulvestrant Therapy We next analyzed the impact of the ESR1 mutant status, detected with the ESR1-ddPCR, in plasma samples collected at baseline and during treatment follow-up. To perform this analysis, we extended the cohort to 60 patients. For each patient, four blood samples were collected: before treatment (D0), after 15 days (D15) and 30 days (D30) of treatment and at the time of progression (ToP). Among the 59 patients screened with contributive results, ESR1 mutations were detected in 17 (28.8%), which is in line with proportions of patients progressing under AI treatment previously reported (8, 9, 11, 24). Out of the 17 patients carrying an ESR1 mutation, 15 had an evaluable PFS (2 patients were withdrawn from the study shortly after the treatment initiation, FIG. 5A). First, we observed no impact of the ESR1 mutational status (mutant vs wild-type) detected at baseline on the PFS. This is in agreement with previous data from the PALOMA-3 trial reporting no improved PFS for patients carrying ESR1 mutations at baseline and treated with fulvestrant (11, 24). After 3 months of treatment, 6 patients presented a disease progression according to RECIST criteria (FIG. 5A). We further analyzed the dynamics of ESR1 mutant copy levels in regards to the 3-months disease progression status (PD versus non-PD). At baseline, we observed a median number of ctDNA copies of 54 per ml of plasma (mean=188.5, range [3-1233]) and there was no apparent association with disease progression at 3 months (FIG. 5B). After 15 days of treatment, we uncovered a dramatic decrease (median=0, mean=14.3, range [0-74]) with 58% (7/12) of patients reaching undetectable ESR1 mutant levels (FIG. 5B). The evolution of the number of ctDNA copies between D0 and D15, for each patient, demonstrates a decrease for all (FIG. 5C). To a minor extent, a significant decrease was also observed on total cfDNA at D15, which was previously described and related to the cytostatic growth arrest triggered by palbociclib (24). At D30, the majority of patients with early disease progression had increased ctDNA levels whereas the majority of patients with longer PFS displayed decreased or stable ctDNA levels (FIG. 5C). Overall, a lower proportion of patients displayed undetectable ctDNA levels (53%=8/15, FIG. 5B), the majority of which (87.5%=7/8) had no early disease progression. Patients with early disease progression had significantly more ctDNA detected at D30 than patients with longer PFS (p<0.0001; FIG. 5D). Only one out of 6 patients with early disease progression had no ctDNA detected whereas only 2 out of 9 patients without early disease progression showed detectable ctDNA (FIG. 5B). This ctDNA positivity at D30 correlates with PFS (p=0.0063; FIG. 5E-F). Here, we show that the detection of ctDNA after 30 days of palbociclib-fulvestrant is a promising dynamic biomarker associated with PFS.

DISCUSSION

The inventors successfully developed a ddPCR assay detecting the most frequent activating ESR1 mutations at once that is compatible with liquid biopsies. By using an unconventional design, which includes a drop-off assay, we targeted, in a single reaction, the E380Q mutation and all the mutations occurring at codons 536 to 540. The multiplex ESR1-ddPCR covers >80% of the currently described ESR1 mutations and >90% of functionally characterized activating ESR1 mutations. Several teams have previously developed ddPCR assays which target only the most frequent ESR1 mutations found in exon 8: D538G, Y537S, Y537N and Y537C (6,21-23). These assays were designed following the conventional ddPCR method containing specific TaqMan probes complementary to each mutant or WT allele. This implies that each mutation is tested in a separate reaction. Thus, multiplex assays were developed to reduce the number of reactions (9, 11). However, these assays cannot identify more than 4 ESR1 mutations in a single reaction and the mutant samples were usually confirmed by singleplex tests (24). To the inventors knowledge, this is the first development pf a ddPCR assay which can detect, in a single reaction, at least eight different mutations in ESR1, namely: E380Q, L536H, L536R, Y537C, Y537N (T>A), Y537N (delinsTA), Y537S and D538G. In addition, the system can identify samples harboring multiple ESR1 mutations (e.g., E380Q combined with one or more mutations in exon 8). Polyclonal ESR1 mutations are well-described events (9,10) and the ESR1-ddPCR assay would be useful in monitoring the dynamics of each mutation during treatment follow up as seen for P-43. The multiplex ESR1-ddPCR assay is highly sensitive, detecting all tested mutations at frequencies lower than 0.19%, an improvement as compared with NGS. They also demonstrated that the ESR1-ddPCR is highly specific by cross-validation with NGS experiments. Lupini et al. recently developed an assay based on an "enhanced-ice-COLD-PCR followed by NGS" with a sensitivity reaching 0.01% (25). However, this ddPCR assay targets specifically the Y537S mutation and involves an enrichment step of the mutant copies preceding the ddPCR assay. Yet, in a context of patient monitoring by liquid biopsy, biological samples are of limited quantity and must be tested rapidly at a low cost. The multiplex ESR1-ddPCR can detect most ESR1 mutations in a single reaction faster and at a lower cost than NGS or any other currently available technology.

Interestingly, it was observed that exons 5 and 8 mutations can be easily distinguished. Moreover, any nucleotide change covered by the Drop-off Ex8 assay can be identified, as confirmed by the detection of the previously unreported mutation Y537N (delinsTA). Furthermore, among exon 8 mutations, the shift in clouds is unique depending on the mutation, indicating if the mutation is more likely to be a D538G or Y537C allele versus mutations in codon 536 or other changes in codon 537. Preclinical data suggest that the Y537S mutation, which accounts for about 10% of all ESR1 mutations, may be less sensitive to fulvestrant than other mutations (12). If this observation is confirmed to be clinically relevant, the ESR1-ddPCR could be used as a first screening tool, since the shift associated to Y537S is distinguishable from the most frequent mutation: D538G, followed by subsequent sequencing of exon 8, to distinguish Y537S from other 536/537 mutations.

The improved analytical sensitivity of the ESR1-ddPCR is particularly useful to monitor ctDNA during treatment follow-up. The inventors demonstrated that ESR1 mutations are good markers for ctDNA dynamics exploration and prediction of treatment response. Indeed, we observed that detection of ctDNA after 30 days of palbociclib-fulvestrant, using the ESR1-ddPCR, correlates with the treatment response and has an impact on PFS.

In conclusion, this method presents the advantage to screen for at least 80% of the ESR1 mutations in a single reaction, as required by large screening studies involving plasma samples.

REFERENCES

1. Li S, Shen D, Shao J, Crowder R, Liu W, Prat A, et al. Endocrine-therapy-resistant ESR1 variants revealed by genomic characterization of breast-cancer-derived xenografts. Cell Rep; 4(6):1116-30 doi S2211-1247(13)00463-4 [pii] 10.1016/j.celrep.2013.08.022.
2. Merenbakh-Lamin K, Ben-Baruch N, Yeheskel A, Dvir A, Soussan-Gutman L, Jeselsohn R, et al. D538G mutation in estrogen receptor-alpha: A novel mechanism for acquired endocrine resistance in breast cancer. Cancer Res; 73(23):6856-64 doi 0008-5472.CAN-13-1197 [pii] 10.1158/0008-5472. CAN-13-1197.
3. Robinson D R, Wu Y M, Vats P, Su F, Lonigro R J, Cao X, et al. Activating ESR1 mutations in hormone-resistant metastatic breast cancer. Nat Genet; 45(12):1446-51 doi ng.2823 [pii] 10.1038/ng.2823.
4. Toy W, Shen Y, Won H, Green B, Sakr R A, Will M, et al. ESR1 ligand-binding domain mutations in hormone-resistant breast cancer. Nat Genet; 45(12):1439-45 doi ng.2822 [pii] 10.1038/ng.2822.
5. Jeselsohn R, Yelensky R, Buchwalter G, Frampton G, Meric-Bernstam F, Gonzalez-Angulo A M, et al. Emergence of constitutively active estrogen receptor-alpha mutations in pretreated advanced estrogen receptor-positive breast cancer. Clin Cancer Res; 20(7):1757-67 doi 10.1158/1078-0432.CCR-13-2332.

6. Takeshita T, Yamamoto Y, Yamamoto-Ibusuki M, Inao T, Sueta A, Fujiwara S, et al. Droplet digital polymerase chain reaction assay for screening of ESR1 mutations in 325 breast cancer specimens. Transl Res; 166(6):540-53 e2 doi S1931-5244(15)00306-0 [pii] 10.1016/j.trsl.2015.09.003.
7 Schiavon G, Hrebien S, Garcia-Murillas I, Cutts R J, Pearson A, Tarazona N, et al. Analysis of ESR1 mutation in circulating tumor DNA demonstrates evolution during therapy for metastatic breast cancer. Sci Transl Med; 7(313):313ra182 doi 7/313/313ra182 [pii] 10.1126/scitranslmed.aac7551.
8. Chandarlapaty S, Chen D, He W, Sung P, Samoila A, You D, et al. Prevalence of ESR1 Mutations in Cell-Free DNA and Outcomes in Metastatic Breast Cancer: A Secondary Analysis of the BOLERO-2 Clinical Trial. JAMA Oncol; 2(10):1310-5 doi 2542919 [pii] 10.1001/jamaoncol.2016.1279.
9. Takeshita T, Yamamoto Y, Yamamoto-Ibusuki M, Tomiguchi M, Sueta A, Murakami K, et al. Analysis of ESR1 and PIK3CA mutations in plasma cell-free DNA from ER-positive breast cancer patients. Oncotarget; 8(32): 52142-55 doi 10.18632/oncotarget. 18479 18479 [pii].
10. Chung J H, Pavlick D, Hartmaier R, Schrock A B, Young L, Forcier B, et al. Hybrid capture-based genomic profiling of circulating tumor DNA from patients with estrogen receptor-positive metastatic breast cancer. Ann Oncol; 28(11):2866-73 doi 4098869 [pii] 10.1093/annonc/mdx490.
11. Fribbens C, O'Leary B, Kilburn L, Hrebien S, Garcia-Murillas I, Beaney M, et al. Plasma ESR1 Mutations and the Treatment of Estrogen Receptor-Positive Advanced Breast Cancer. J Clin Oncol; 34(25):2961-8 doi JCO.2016.67.3061 [pii] 10.1200/J C0.2016.67.3061.
12. Toy W, Weir H, Razavi P, Lawson M, Goeppert A U, Mazzola A M, et al. Activating ESR1 Mutations Differentially Affect the Efficacy of E R Antagonists. Cancer Discov; 7(3):277-87 doi 2159-8290.CD-15-1523 [pii] 10.1158/2159-8290.CD-15-1523.
13. Decraene C, Silveira A B, Bidard F C, Vallee A, Michel M, Melaabi S, et al. Multiple Hotspot Mutations Scanning by Single Droplet Digital PCR. Clin Chem; 64(2):317-28 doi clinchem.2017.272518 [pii] 10.1373/clinchem.2017.272518.
14. Seki Y, Fujiwara Y, Kohno T, Takai E, Sunami K, Goto Y, et al. Picoliter-Droplet Digital Polymerase Chain Reaction-Based Analysis of Cell-Free Plasma DNA to Assess EGFR Mutations in Lung Adenocarcinoma That Confer Resistance to Tyrosine-Kinase Inhibitors. Oncologist; 21(2):156-64 doi theoncologist.2015-0288 [pii] 10.1634/theoncologist.2015-0288.
15. Bidshahri R, Attali D, Fakhfakh K, McNeil K, Karsan A, Won J R, et al. Quantitative Detection and Resolution of BRAF V600 Status in Colorectal Cancer Using Droplet Digital PCR and a Novel Wild-Type Negative Assay. J Mol Diagn; 18(2):190-204 doi S1525-1578(15)00262-7 [pii] 10.1016/j.jmoldx.2015.09.003.
16. Niu J, Andres G, Kramer K, Kundranda M N, Alvarez R H, Klimant E, et al. Incidence and clinical significance of ESR1 mutations in heavily pretreated metastatic breast cancer patients. Onco Targets Ther; 8:3323-8 doi 10.2147/OTT.S92443 ott-8-3323 [pii].

17. Zonta E, Garlan F, Pecuchet N, Perez-Toralla K, Caen O, Milbury C, et al. Multiplex Detection of Rare Mutations by Picoliter Droplet Based Digital PCR: Sensitivity and Specificity Considerations. PLoS One; 11(7):e0159094 doi 10.1371/journal.pone.0159094 PONE-D-16-13557 [pii].

18. Milbury C A, Zhong Q, Lin J, Williams M, Olson J, Link D R, et al. Determining lower limits of detection of digital PCR assays for cancer-related gene mutations. Biomol Detect Quantif; 1(1):8-22 doi 10.1016/j.bdq.2014.08.001 S2214-7535(14)00004-7 [pii].

19. Madic J, Kiialainen A, Bidard F C, Birzele F, Ramey G, Leroy Q, et al. Circulating tumor DNA and circulating tumor cells in metastatic triple negative breast cancer patients. Int J Cancer; 136(9):2158-65 doi 10.1002/ijc.29265.

20. Lebofsky R, Decraene C, Bernard V, Kamal M, Blin A, Leroy Q, et al. Circulating tumor DNA as a non-invasive substitute to metastasis biopsy for tumor genotyping and personalized medicine in a prospective trial across all tumor types. Mol Oncol; 9(4):783-90 doi S1574-7891(14)00288-9 [pii] 10.1016/j.molonc.2014.12.003.

21. Clatot F, Perdrix A, Augusto L, Beaussire L, Delacour J, Calbrix C, et al. Kinetics, prognostic and predictive values of ESR1 circulating mutations in metastatic breast cancer patients progressing on aromatase inhibitor. Oncotarget; 7(46):74448-59 doi 12950 [pii] 10.18632/oncotarget.12950.

22. Gyanchandani R, Kota K J, Jonnalagadda A R, Minteer T, Knapick B A, Oesterreich S, et al. Detection of ESR1 mutations in circulating cell-free DNA from patients with metastatic breast cancer treated with palbociclib and letrozole. Oncotarget; 8(40):66901-11 doi 10.18632/oncotarget.11383 11383 [pii].

23. Wang P, Bahreini A, Gyanchandani R, Lucas P C, Hartmaier R J, Watters R J, et al. Sensitive Detection of Mono- and Polyclonal ESR1 Mutations in Primary Tumors, Metastatic Lesions, and Cell-Free DNA of Breast Cancer Patients. Clin Cancer Res; 22(5):1130-7 doi 1078-0432.CCR-15-1534 [pii] 10.1158/1078-0432.CCR-15-1534.

24. O'Leary B, Hrebien S, Morden J P, Beaney M, Fribbens C, Huang X, et al. Early circulating tumor DNA dynamics and clonal selection with palbociclib and fulvestrant for breast cancer. Nat Commun; 9(1):896 doi 10.1038/s41467-018-03215-x 10.1038/541467-018-03215-x [pii].

25. Lupini L, Moretti A, Bassi C, Schirone A, Pedriali M, Querzoli P, et al. High-sensitivity assay for monitoring ESR1 mutations in circulating cell-free DNA of breast cancer patients receiving endocrine therapy. Sci Rep; 8(1):4371 doi 10.1038/541598-018-22312-x 10.1038/541598-018-22312-x [pii].

LIST OF ABBREVIATIONS

Aromatase Inhibitor (AI)
Cell-free DNA (cfDNA)
Circulating tumor DNA (ctDNA)
Droplet digital PCR (ddPCR)
ER+ HER2-negative Metastatic Breast Cancer (ER+ HER2− MBC)
Estrogen Receptor (ER)
Estrogen Receptor positive (ER+)
Limit of blank (LOB)
Limit of detection (LOD)
Mutant Allele Frequency (MAF)
Peripheral blood mononuclear cells (PBMC)
Standard deviation (SD)
Progressive disease (PD)
Wild type (WT)
Human Genes:
ESR1: Estrogen Receptor 1
HER2: Human Epidermal Growth Factor Receptor 2
EGFR: Epithelial Growth Factor Receptor
KRAS: KRAS proto-oncogene, GTPase
BRAF: B-Raf Proto-Oncogene, Serine/Threonine kinase

The invention claimed is:

1. An in vitro method for identifying, characterizing and discriminating individual mutations in a hotspot mutation sequence of a first and a second ESR1 target fragment from a DNA sample, said method comprising subjecting the DNA sample to a drop-off digital polymerase chain reaction (PCR) in the presence of a PCR solution comprising:

a pair of primers suitable for amplifying the first ESR1 target fragment;

an oligonucleotide reference (REF) hydrolysis probe, labeled with a fluorophore, wherein said REF oligonucleotide probe is complementary to a wild-type sequence of the first ESR1 target fragment located outside of the hotspot mutation sequence; and an oligonucleotide hotspot (HOTSPOT) hydrolysis probe, labeled with another fluorophore, wherein said oligonucleotide HOTSPOT probe is complementary to a wild-type sequence of the hotspot mutation sequence of the first ESR1 target fragment, and, wherein the drop-off digital PCR is combined with a mutation-specific digital PCR for identifying a mutation in a hotspot mutation sequence of the second ESR1 target fragment from said DNA sample; and wherein the PCR solution further comprises:

a pair of primers suitable for amplifying the second ESR1 target fragment of the DNA sample;

an oligonucleotide hydrolysis probe (MS-MUT), labeled with a fluorophore, wherein said oligonucleotide MS-MUT probe is complementary to of the hotspot mutation sequence of the second ESR1 target fragment; and an oligonucleotide reference (MS-REF) hydrolysis probe, labeled with another fluorophore, wherein the MS-REF oligonucleotide probe is complementary to a wild-type sequence of the second ESR1 target fragment located outside of the hotspot mutation sequence of the second ESR1 target fragment.

2. The method according to claim 1, wherein the first ESR1 target fragment is from the ligand binding domain of ESR1.

3. The method according to claim 2, wherein the first ESR1 target fragment of the DNA sample is exon 8.

4. The method according to claim 3, wherein the hotspot mutation sequence in the first ESR1 target fragment includes codons 536-538 of exon 8.

5. The method according to claim 1, wherein the second ESR1 target fragment is exon 5.

6. The method according to claim 5, wherein the hotspot mutation sequence of the second ESR1 target fragment includes codon 380.

7. The method according to claim 6, wherein the hotspot mutation sequence of the second ESR1 target fragment corresponds to E380Q.

8. The method according to claim 1, wherein the fluorophore associated with the REF probe is identical to the fluorophore associated with the MS-MUT probe and wherein the fluorophore associated with the HOTSPOT probe is identical to the fluorophore associated with the MS-REF probe.

9. The method according to claim 1, wherein the ESR1 target fragments are from genomic tumor DNA.

10. The method according to claim 1, wherein the DNA sample is selected from the group consisting of tumor tissue, disseminated cells, feces, blood cells, blood plasma, serum, lymph nodes, urine, saliva, semen, sputum, cerebrospinal fluid, tears, mucus, pancreatic juice, gastric juice, amniotic fluid, and serous fluids.

11. The method according to claim 1, wherein the DNA sample is from a subject suffering from advanced breast cancer.

12. The method according to claim 1, wherein the DNA sample is from a subject suffering from ER-positive breast cancer after the development of acquired secondary resistance to aromatase inhibitors.

13. The method according to claim 1, wherein the nucleotide sequences of the pair of primers suitable for amplifying the first ESR1 target fragment of the DNA sample consist of SEQ ID NO: 3 and SEQ ID NO: 4, the nucleotide sequence of the oligonucleotide reference (REF) hydrolysis probe consists of SEQ ID NO: 7; and the nucleotide sequence of the oligonucleotide hotspot (HOTSPOT) hydrolysis probe consists of SEQ ID NO: 8.

14. The method according to claim 1, wherein the nucleotide sequences of the pair of primers suitable for amplifying said second ESR1 target fragment of the DNA sample consist of SEQ ID NO: 1 and SEQ ID NO: 2, the nucleotide sequence of the oligonucleotide hydrolysis probe (MS-MUT) consists of SEQ ID NO: 6; and the nucleotide sequence of the oligonucleotide reference (MS-REF) hydrolysis probe consists of SEQ ID NO: 5.

\* \* \* \* \*

SEQUENCE LISTING

```
<160> NUMBER OF SEQ ID NOS: 13

<210> SEQ ID NO 1
<211> LENGTH: 24
<212> TYPE: DNA
<213> ORGANISM: Artificial Sequence
<220> FEATURE:
<223> OTHER INFORMATION: Synthetic Sequence

<400> SEQUENCE: 1
ttgcttgttt tcaggctttg tgga                                    24

<210> SEQ ID NO 2
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 2
agcgccagac gagaccaatc at                                      22
```

-continued

```
<210> SEQ ID NO 3
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 3
acagcatgaa gtgcaagaac gt                                              22

<210> SEQ ID NO 4
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 4
tggctttggt ccgtctcctc                                                20

<210> SEQ ID NO 5
<211> LENGTH: 15
<212> TYPE: DNA
<213> ORGANISM: Artificial Sequence
<220> FEATURE:
<223> OTHER INFORMATION: Synthetic Sequence

<400> SEQUENCE: 5
tgaccctcca tgatc                                                     15

<210> SEQ ID NO 6
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 6
accttctaca atgtgcctg                                                 19

<210> SEQ ID NO 7
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 7
ctagccgtgg aggggc                                                    16

<210> SEQ ID NO 8
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 8
cctctatgac ctgctgc                                                   17

<210> SEQ ID NO 9
<211> LENGTH: 17
<212> TYPE: DNA
<213> ORGANISM: Artificial Sequence
<220> FEATURE:
<223> OTHER INFORMATION: Synthetic Sequence
```

-continued

```
<400> SEQUENCE: 9
ccgctatgac ctgctgc                                                    17

<210> SEQ ID NO 10
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 10
cctcaatgac ctgctgc                                                    17

<210> SEQ ID NO 11
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 11
cctctctgac ctgctgc                                                    17

<210> SEQ ID NO 12
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 12
cctctgtgac ctgctgc                                                    17

<210> SEQ ID NO 13
<211> LENGTH: 17
<212> TYPE: DNA
<213> ORGANISM: Artificial Sequence
<220> FEATURE:
<223> OTHER INFORMATION: Synthetic Sequence

<400> SEQUENCE: 13
cctctatggc ctgctgc                                                    17
```